(12) United States Patent
Kyomoto et al.

(10) Patent No.: US 9,044,323 B2
(45) Date of Patent: Jun. 2, 2015

(54) HIGH WEAR-RESISTANT BEARING MATERIAL AND ARTIFICIAL JOINT REPLACEMENT USING THE SAME

(75) Inventors: Masayuki Kyomoto, Tokyo (JP); Toru Moro, Tokyo (JP); Kazuhiko Ishihara, Tokyo (JP); Tomohiro Konno, Tokyo (JP); Kozo Nakamura, Tokyo (JP); Yoshio Takatori, Tokyo (JP); Hiroshi Kawaguchi, Tokyo (JP); Hiroaki Takadama, Aichi (JP); Makoto Kondo, Osaka (JP); Noboru Yamawaki, Osaka (JP); Takeshi Nizuka, Osaka (JP); Masami Hashimoto, Aichi (JP)

(73) Assignee: KYOCERA MEDICAL CORPORATION, Osaka (JP)

( * ) Notice: Subject to any disclaimer, the term of this patent is extended or adjusted under 35 U.S.C. 154(b) by 1204 days.

(21) Appl. No.: 12/223,669

(22) PCT Filed: Feb. 5, 2007

(86) PCT No.: PCT/JP2007/051923
§ 371 (c)(1),
(2), (4) Date: Dec. 29, 2008

(87) PCT Pub. No.: WO2007/091521
PCT Pub. Date: Aug. 16, 2007

(65) Prior Publication Data
US 2009/0306781 A1  Dec. 10, 2009

(30) Foreign Application Priority Data

Feb. 6, 2006  (JP) .................................. 2006-028529
Dec. 15, 2006  (JP) .................................. 2006-338601

(51) Int. Cl.
*A61F 2/30* (2006.01)
*A61F 2/46* (2006.01)
(Continued)

(52) U.S. Cl.
CPC ............... *A61F 2/30767* (2013.01); *A61F 2/32* (2013.01); *A61F 2/34* (2013.01); *A61F 2/36* (2013.01);
(Continued)

(58) Field of Classification Search
CPC ......... A61F 2/38; A61F 2/32; A61F 2/30767; A61F 2/3094; A61F 2220/0025; A61F 2220/0033; A61L 27/34; A61L 27/50
USPC ................................... 623/23.59, 23.58, 926
See application file for complete search history.

(56) References Cited

U.S. PATENT DOCUMENTS 3,990,118 A * 11/1976 Strickland et al. .......... 623/23.39
4,059,854 A * 11/1977 Laure .......................... 623/21.16
(Continued)

FOREIGN PATENT DOCUMENTS

EP    1 206 946    5/2002
EP    1 211 268    6/2002
(Continued)

OTHER PUBLICATIONS

International Search Report issued Mar. 20, 2007 in the International (PCT) Application of which the present application is the U.S. National Stage (in English).
(Continued)

*Primary Examiner* — Paul Prebilic
(74) *Attorney, Agent, or Firm* — Wenderoth, Lind & Ponack, L.L.P.

(57) ABSTRACT

The present invention provides a bearing material that is excellent in durability and is capable of maintaining wear resistance over a long period of time. The bearing material of the present invention is a high wear-resistance bearing material 10 for being used under a humid environment comprising: a base body 12 made of a polymer material having a methylene group; and a polymer layer 30 covering a bearing surface 16 of the substrate 12, the polymer layer 30 comprising polymer chains which have a phosphorylcholine group and are grafted from the bearing surface 16, wherein a phosphoric index of the sliding surface 16 which is calculated by dividing a peak intensity of phosphate group in an infrared spectrum measured on the sliding surface by a peak intensity of the methylene group therein is not less than 0.28.

24 Claims, 24 Drawing Sheets

(51) Int. Cl.
*A61L 27/34* (2006.01)
*A61L 27/50* (2006.01)
*A61F 2/32* (2006.01)
*A61F 2/34* (2006.01)
*A61F 2/36* (2006.01)
*A61F 2/38* (2006.01)
*A61F 2/40* (2006.01)
*A61F 2/42* (2006.01)
*A61F 2/44* (2006.01)

(52) U.S. Cl.
CPC .............. *A61F 2/3662* (2013.01); *A61F 2/367* (2013.01); *A61F 2/3676* (2013.01); *A61F 2/38* (2013.01); *A61F 2/3804* (2013.01); *A61F 2/3859* (2013.01); *A61F 2/389* (2013.01); *A61F 2/40* (2013.01); *A61F 2/4059* (2013.01); *A61F 2/4081* (2013.01); *A61F 2/4202* (2013.01); *A61F 2/4241* (2013.01); *A61F 2/4425* (2013.01); *A61F 2/468* (2013.01); *A61F 2002/3065* (2013.01); *A61F 2002/30654* (2013.01); *A61F 2002/30884* (2013.01); *A61F 2002/30904* (2013.01); *A61F 2002/30934* (2013.01); *A61F 2002/3493* (2013.01); *A61F 2002/3611* (2013.01); *A61F 2002/3625* (2013.01); *A61F 2002/3631* (2013.01); *A61F 2002/3682* (2013.01); *A61F 2002/4018* (2013.01); *A61F 2002/4051* (2013.01); *A61F 2002/4062* (2013.01); *A61L 27/34* (2013.01); *A61L 27/50* (2013.01)

(56) References Cited

U.S. PATENT DOCUMENTS

| | | | |
|---|---|---|---|
| 5,879,400 | A | 3/1999 | Merrill et al. |
| 6,228,900 | B1 | 5/2001 | Shen et al. |
| 6,464,926 | B1 | 10/2002 | Merrill et al. |
| 6,641,617 | B1 | 11/2003 | Merrill et al. |
| 6,653,423 | B1 | 11/2003 | Yamamoto et al. |
| 6,786,933 | B2 | 9/2004 | Merrill et al. |
| 6,828,028 | B1 | 12/2004 | Fukui et al. |
| 7,785,372 | B2 * | 8/2010 | Ishihara et al. ............ 623/23.59 |
| 2002/0007219 | A1 | 1/2002 | Merrill et al. |
| 2002/0156536 | A1 | 10/2002 | Harris et al. |
| 2003/0013781 | A1 | 1/2003 | Merrill et al. |
| 2003/0105182 | A1 | 6/2003 | Merrill et al. |
| 2003/0119935 | A1 | 6/2003 | Merrill et al. |
| 2004/0132856 | A1 | 7/2004 | Merrill et al. |
| 2004/0243249 | A1 | 12/2004 | Ishihara et al. |
| 2005/0006821 | A1 | 1/2005 | Merrill et al. |
| 2005/0010288 | A1 | 1/2005 | Merrill et al. |
| 2005/0056971 | A1 | 3/2005 | Merrill et al. |
| 2005/0096749 | A1 | 5/2005 | Marrill et al. |
| 2005/0165495 | A1 | 7/2005 | Merrill et al. |
| 2005/0267594 | A1 | 12/2005 | Merrill et al. |
| 2009/0105364 | A1 | 4/2009 | Merrill et al. |
| 2009/0306781 | A1 * | 12/2009 | Kyomoto et al. .......... 623/18.11 |

FOREIGN PATENT DOCUMENTS

| | | |
|---|---|---|
| EP | 1 433 488 | 6/2004 |
| JP | 2984203 | 9/1999 |
| JP | 2003-310649 | 11/2003 |
| JP | 2005-237629 | 9/2005 |
| WO | 97/29793 | 8/1997 |
| WO | 01/05855 | 1/2001 |
| WO | 03/070289 | 8/2003 |

OTHER PUBLICATIONS

International Preliminary Report on Patentability issued Oct. 9, 2008 in the International (PCT) Application of which the present application is the U.S. National Stage (in English).

Written Opinion of the International Searching Authority issued Mar. 20, 2007 in the International (PCT) Application of which the present application is the U.S. National Stage (with partial English translation).

Toru Moro, et al., "Surface grafting of artificial joints with a biocompatible polymer for preventing periprosthetic osteolysis," Nature Materials, 2004, vol. 3, No. 11, pp. 829-836.

Toru Moro, "Nano-hyomen seigyo ni yoru atarashii jinko kokansetsu no kaihatsu," Rheumatology, 2005, vol. 33, No. 6, pp. 639-645 (with partial English translation).

Toru Moro et al:, "Shinsozai ni yoru jinko kokansetsu no kaihatsu," Orthopaedic Surgery and Traumatology, 2005, vol. 48, No. 3, pp. 245-250 (with partial English translation).

Kazuhiko Ishihara et al., "Jinko saibomaku hyomen kochiku ni yoru chokino jinko kansetsu no kaihatsu," Materials Science and Technology, 2005, vol. 142, No. 4, pp. 178-182 (with partial English translation).

Toru Moro, "Seitaitekigosei polymer no nano-hyomen syori ni yoru jinko kokansetsu no yurumi no soshi," Journal of Japanese Society for Biomaterials, 2005, vol. 23, No. 6, pp. 407-412 (with partial English translation).

Toru Moro et al., "Polyethylene liner hyomen no MPC shori wa jinko kokansetsu no yurumi wo yokusei suru: nano-hyomen seigyo ni yoru chojumyo jinko kokansetsu no kaihatsu," Hip Joint, 2005, vol. 31, pp. 469-474 (with partial English translation).

Toru Moro et al., "Saikin no shinpo," The Japanese Journal of Artificial Organs, 2005, vol. 34, No. 3, pp. 166-170 (with partial English translation).

Toru Moro, "Polymer Nano Graft Hyomen Kochiku o Kiban to shita Taimamo Jinko Kokansetsu no Sosei", Journal of Japanese Society for Biomaterials, Apr. 2006, vol. 24, No. 2, pp. 108 to 114.

K. Ishihara et al, "Photoinduced graft polymerization of 2-methacryloyloxyethyl phosporylcholine on polyethylene membrane surface for obtaining blood cell adhesion resistance", Colloids and Surfaces. B, Biointerfaces, 2000, vol. 18, pp. 325-335.

* cited by examiner

HIGH WEAR-RESISTANT BEARING MATERIAL AND ARTIFICIAL JOINT REPLACEMENT USING THE SAME

BACKGROUND OF THE INVENTION

1. Field of the Invention

The present invention relates to a high wear-resistant bearing material to be used under a humid environment, and particularly to a bearing material used in artificial joint as a prosthesis for a joint of human body.

2. Description of the Related Art

Ultra-high molecular weight polyethylene (hereafter referred to as UHMWPE) is used as a common material to form a bearing material that constitutes the sliding surface of an artificial knee joint such as artificial hip joint or artificial knee joint. However, wear debris of UHMWPE generated by frictional motion of the artificial joint used in the human body has a potential of inducing osteolysis. A decrease in the bonding force between the artificial joint and bone, the so-called loosening, caused by osteolysis has been a focus of great concern as a complication of joint arthroplasty. Linear wear of UHMWPE is usually from about 0.1 mm to 0.2 mm annually, which does not pose a problem for some time after undergoing the joint arthroplasty, although the loosening becomes significant after a period of about five years. Then the artificial joint needs to be replaced, thus placing a great burden on the patient.

One measure to avoid the loosening is to reduce the amount of the wear debris generated from the UHMWPE. For this purpose, various attempts have been made such as seeking better combination of materials to make the joint surface and improvement of the material itself. These attempts include the vigorous researches conducted on UHMWPE of which molecular chain is crosslinked through irradiation with electron beam or gamma ray (crosslinked polyethylene, hereafter referred to as CLPE) (for example, specification of Japanese Patent No. 2,984,203, specification of U.S. Pat. No. 6,228,900 and International Publication No. WO 97/29793, pamphlet). These researches are based on the fact that irradiation of a polymer material with high energy beams such as electron beam or gamma-ray generates free radicals due to scission of molecular chains, followed by recombination of a molecular chain and a crosslinking reaction. The CLPE has higher wear resistance than the conventional UHMWPE, and it has been reported that the wear can be decreased to one fifth or as small as one tenth that of the conventional material.

Many research efforts have also been directed to the improvement of tribological characteristic of the surface of the bearing material through the formation of a film layer on the UHMWPE. For example, such a technique has been known that a film of a random copolymer having allylamine and a phosphorylcholine analogous group is fixed onto the material surface used for a medical purpose that is required to have excellent tribological characteristic such as artificial joint, so as to render biocompatibility and surface lubrication (for example, International Publication No. WO 01/05855, pamphlet).

Particularly high effect of suppressing wear of the artificial joint can be achieved by grafting a polymerizable monomer having a phosphorylcholine group onto the bearing surface of an artificial joint made of UHMWPE, thus providing an artificial joint component made of a polymer material that has a remarkable effect of suppressing wear of the artificial joint and is capable of suppressing the generation of wear debris (for example, Japanese Patent Unexamined Publication (Kokai) No. 2003-310649).

Even when the bearing surface of a joint replacement is modified to make it resistant to wear, the technologies currently available are not capable of completely prevent wear of the bearing surface. Thus the bearing material of a joint replacement with the surface modified by the prior art technology may demonstrate high wear resistance in the initial stage of use, but would show rapidly deteriorating wear resistance once the modified surface region has been removed by wear or delamination over a long period of use. Then, if the decreasing wear resistance leads to the generation of wear debris, the possibility is high for loosening to take place.

The bearing material of a joint replacement made by using the CLPE has a short history of clinical application, and therefore it has not been verified whether its wear resistance would be maintained over an extended period of time.

In case the technique of fixing a film of a random copolymer onto the material surface used for a medical purpose is applied to a bearing material of a joint replacement, the film made of a random copolymer is subjected to severe friction that causes wear and is quite likely to remove the UHMWPE surface. Thus it is difficult to apply this technology into practical use.

Such a remove occurs because of weak bonding strength between the UHMWPE surface and the random copolymer layer. The bonding strength is weak partly because the random copolymer layer in which polymerization has progressed to a significant level is fixed onto the UHMWPE surface, and partly because of the absence on the UHMWPE surface of a functional group that enables it to bond with the polymerized random copolymer layer.

In contrast, Japanese Patent Unexamined Publication (Kokai) No. 2003-310649 describes a technology that successfully increased the bonding strength between a polymer chain having a phosphorylcholine group and UHMWPE surface by grafting a polymer chain having a phosphorylcholine group and the surface of a UHMWPE substrate. This enabled it to obtain a bearing material of a joint replacement having sliding surface made of UHMWPE whereon a high wear-resistant film, that does not remove even when used under harsh friction and wear conditions, is formed. However, it has not been verified whether the wear resistance of this bearing material of a joint replacement would be maintained over an extended period of time. For example, Japanese Patent Unexamined Publication (Kokai) No. 2003-310649 describes an accelerated joint simulator wear test in which a stainless steel ball against the bearing material of a joint replacement was performed up to three million cycles, which is equivalent to three years of use and does not prove the high wear-resistance during use over the lifetime typically required of an artificial joint (for example, five years).

SUMMARY OF THE INVENTION

With the background described above, an object of the present invention is to provide a bearing material that is excellent in durability and is capable of maintaining high wear-resistance over a long period of time, and a method for manufacturing the same.

The present inventors has completed a bearing material for artificial joint of the present invention based on a finding that, in case a polymer layer having a phosphorylcholine repeating unit is grafted from a UHMWPE surface, high wear-resistance of the layer depends on the thickness of the polymer layer and there is an optimum range of the thickness.

The bearing material of the present invention is a high wear-resistance bearing material to be used under a humid environment, wherein the bearing material comprises the substrate made of a polymer material having a methylene repeating unit; and a polymer layer covering a bearing surface of the substrate, the polymer layer comprising polymer chains which have a phosphorylcholine group and are grafted from the sliding surface, wherein the polymer layer has a thickness of 10 to 200 nm.

The bearing material of the present invention can suppress the wear to a low level even when used under harsh frictional conditions over a long period of time, and therefore reduces the possibility of causing osteolysis that is induced by wear debris. Also because the joint replacement is unlikely to undergo a change in the shape of the bearing surface over an extended period of time, performance of the artificial joint as designed can be maintained. As a result, once joint arthroplasty is conducted, since the artificial joint maintains stable function over a long period of time, the number of replacement surgeries required for the artificial joint can be reduced or the need thereof can be eliminated altogether. Also because the bearing material exhibits high wear-resistance in a humid environment other than that of human body, it is suitable for other applications to bearing material for being used under frictional conditions.

The present invention also provides a method for producing a bearing material, which comprises the steps of forming the substrate made of the polymer material having the methylene repeating unit; and forming the polymer layer on the bearing surface of the surface by being grafted from the bearing surface with the polymer chains including the phosphorylcholine group, the step of forming the polymer layer comprising processes of: applying a photoinduced polymerization initiator on the bearing surface of the substrate; and irradiating the bearing surface of the substrate to a ultraviolet light having an sufficient intensity so as to excite the photoinduced polymerization initiator with the substrate being immersed in a solution including a polymerizable monomer having the phosphorylcholine group, wherein the solution including the polymerizable monomer has a monomer concentration of 0.25 to 0.50 mol/L.

According to the present invention, a uniform polymer layer having a favorable thickness can be formed by controlling the monomer concentration in feed.

According to the present invention, there can be provided a bearing material: excellent in durability and is capable of maintaining high wear-resistance over a long period of time.

DESCRIPTION OF REFERENCE NUMERALS

Figure 1:
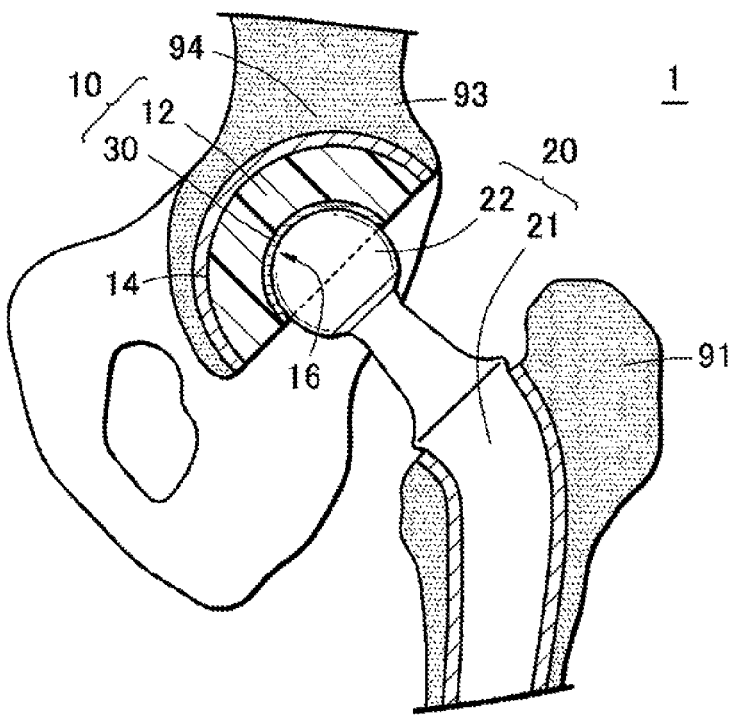
FIG. 1 is a schematic diagram of an artificial hip joint according to a first embodiment of the present invention.

1 Artificial hip joint
10 Acetabular cup
12 Cup substrate
15 Glenoid cavity cup
16 Covered sliding surface
20 Femoral stem
22 Femoral head
27 Humeral head
30 Polymer layer
32 Artificial vertebral joint
33 Upper component
36 Convex bearing component
40 Bipolar femoral head
46 Liner substrate
48 Tibial tray
52 Femoral component
54 Ulnar tray
62 Humeral component
64 Tibial tray
68 Ankle bone component 70 Artificial shoulder joint
72 Artificial knee joint
74 Artificial elbow joint
76 Artificial ankle joint
80 Artificial finger joint
82 Shaft part
86 Bearing component

DETAILED DESCRIPTION OF THE INVENTION

First Embodiment

FIG. 1 is a schematic diagram of an example of artificial joint, an artificial hip joint 1. The artificial hip joint 1 is constituted from a bearing component (acetabular cup) 10 that is fixed onto acetabulum 94 of a hip bone 93 and a femoral stem 20 that is fixed onto a proximal end of a femur 91. The acetabular cup 10 comprises a cup substrate 12 that has a substantially semi-spherical acetabulum fixing surface 14 and a bearing surface of concave semi-spherical shape, and a polymer layer 30 with which the sliding surface is covered. A bone head 22 of a femoral stem 20 is slidably fitted to a covered bearing surface 16 of the acetabular cup 10, so as to function as a hip joint.

Figure 2:
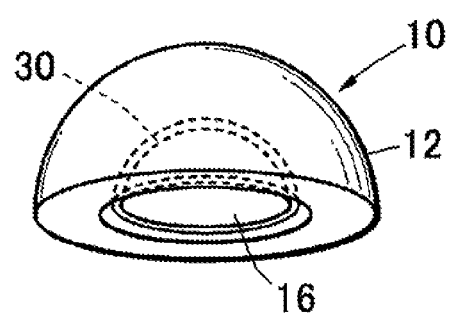
FIG. 2 is a perspective view of an acetabular cup for the artificial hip joint according to a first embodiment of the present invention.

As shown in FIG. 1 and FIG. 2, the acetabular cup 10 of the present invention is constituted by graft-coating the bearing surface of the cup substrate 12 with a polymer layer 30 having a phosphorylcholine group. The polymer layer 30 has such a molecular structure as polymer chains having a phosphorylcholine group are orientational ordered along the surface. This structure resembles that of cell membrane.

A biolayer that constitutes the cartilage surface of a joint in the living body is an aggregate of phospholipid molecules, and has microscopic surface structure of being covered with phosphorylcholine groups (Ishihara; Surgery, Vol. 61, p 122, 1999). The biolayer holds a lubricating liquid therein so as to constitute a lubricated joint surface having an extremely low friction coefficient. The polymer layer 30 of the present invention also has affinity with the lubricating liquid and is capable of holding the lubricating liquid therein similarly to the biolayer, so as to provide a lower friction coefficient than that of the covered sliding surface 16 of the acetabular cup 10 of the prior art.

Tribological characteristic can be improved so as to provide higher wear-resistance by covering the bearing surface of the acetabular cup 10 with the polymer layer 30 having a phosphorylcholine group, as described above. However, the bearing component for artificial joint is required to maintain the high wear-resistance over a long period of time in such a harsh operating condition as sliding while supporting the entire body weight in the state of making contact with the body fluid. In other words, extremely high durability is required.

Accordingly, the present inventors have studied the dependency of durability of the acetabular cup 10 on the thickness of the polymer layer 30. It was found that excellent wear resistance is obtained when the thickness of the polymer layer is in a range from 10 to 200 nm. When the film thickness is less than 10 nm, durability deteriorates in a short period of time due to insufficient wear resistance. When the film thickness is larger than 200 nm, uniformity of the polymer layer 30 tends to deteriorate and the film may have portions where the film is thinner or missing. The polymer layer 30 may remove or the acetabular cup 10 may wear off in such portions, thus resulting in deterioration of wear resistance. Particularly preferable range of the thickness of the polymer layer 30 is in a range from 30 to 100 nm.

When durability of the acetabular cup 10 is improved, generation of wear debris can be suppressed over a long period of time, thus suppressing the occurrence of loosening. As a result, it is made possible to provide the artificial joint that makes it possible for the number of replacement surgeries for the artificial joint to be reduced or eliminated altogether.

The present inventors also paid attention to the density of the polymer layer 30 in an attempt to improve the durability of the acetabular cup 10. In the present invention, density of the polymer layer means the number of 2-methacryloyloxyethyl phosphorylcholine (hereinafter referred to as MPC) polymer that exists in a unit area. When the thickness of the MPC polymer layer is small enough, however, the density may be used as an indication of denseness of the MPC polymer in a unit area. Thus it can be regarded that the higher the density, the more the MPC polymer is crowded on the bearing surface of the acetabular cup.

In the present invention, a new concept of a phosphoric index is introduced as a unit to define the density of the polymer layer 30, thereby quantitatively defining the durability and density of the polymer layer. A phosphoric index is defined as the ratio $I_P/I_M$ of peak intensity $I_P$ at 1080 m$^{-1}$ that is the absorption wavelength of a phosphate group to a peak intensity $I_M$ at 1,460 m$^{-1}$ that is the absorption wavelength of a methylene repeating unit in the spectrum of Fourier transform infrared spectroscopy (FT-IR).

When the polymer layer 30 having a phosphorylcholine group is formed on the cup substrate 12 made of a polymer material having a methylene repeating unit as in the present invention and FT-IR measurement is carried out, the absorption peak of methylene repeating unit due to the cup substrate 12 and the absorption peak of phosphate group due to the polymer layer 30 are observed. Provided that the cup substrate 12 is constant and the thickness of the polymer layer 30 does not undergo an excessive variation (for example, deviation in thickness remains within 1 μm), phosphoric index calculated from the two peak intensities is roughly proportional to a number of phosphate group s existing in unit area of the cup substrate 12.

The phosphoric index was used to evaluate the durability of the acetabular cup 10 provided with the polymer layer 30 having a phosphorylcholine group on the bearing surface. It was found that the acetabular cup having the polymer layer 30 of the thickness from 10 to 200 nm with phosphoric index not lower than 0.32 showed significantly higher durability than the acetabular cup of the prior art, and accelerated joint simulator wear test indicated durability of five years or more. Furthermore, experiments with acetabular cups having phosphoric index of 0.45 or higher exhibited durability of 10 years or more. These values of durability may be regarded as lifetime that is long enough to eliminate the need of revision surgery over lifetime for patients who receive joint arthroplasty at ages over a certain level.

In order to achieve such a high durability of the acetabular cup 10, phosphoric index of the polymer layer 30 is preferably 0.32 or more, and more preferably 0.45 or more.

The polymer layer 30 having high hydrophilicity is considered to show good compatibility with the lubricating liquid in the human body. Once fully impregnated with the lubricating liquid, the polymer layer 30 would enable the covered bearing surface 16 of the acetabular cup 10 to make smooth sliding motion, thereby improving the durability of the acetabular cup 10. The hydrophilicity can be adjusted by controlling the density of the polymer layer 30. Accordingly, the present inventors investigated the relationship between the phosphoric index and hydrophilicity and between durability and hydrophilicity. Hydrophilicity (static-water contact angle) is evaluated by the contact angle of the polymer layer 30 with a water droplet placed thereon.

The polymer layer 30 having a phosphorylcholine group tends to show higher hydrophilicity and a smaller static-water contact angle when a phosphoric index increases. However, as the phosphoric index increases beyond 0.3, a contact angle takes a minimum value of 14° and do not decrease anymore when the phosphoric index is increased further.

With regard to durability, the accelerated joint simulator wear test produced the following findings. In the acetabular cup 10 that was estimated to have durability to last five years, which is regarded as sufficiently long for clinical application, the polymer layer 30 showed static-water contact angle of 20° or less in terms of a static-water contact angle. In the acetabular cup 10 that was estimated to have durability to last as long as ten years or more, the polymer layer 30 showed 14° or less static-water contact angle. These results show that the static-water contact angle of the polymer layer 30 is preferably 20° or less, more preferably 14° or less. In this way, durability of the acetabular cup can be improved so as to suppress wear debris from being generated over a long period of time, thereby providing an artificial joint that suppresses loosening from occurring and makes it possible for the number of replacement surgeries required for the artificial joint to be reduced or eliminated altogether.

Manufacture of the bearing material of the present invention requires it to fix the polymer layer 30 to the bearing surface of the acetabular cup 10. While several methods of fixing have been known, the present invention employs photoinduced graft polymerization by means of ultraviolet-ray irradiation. That is, the polymer layer 30 is fixed by bonding between a polymerizable monomer having a phosphorylcholine group and the bearing surface. This method has such advantages as the capability to modify only the bearing surface without causing the properties such as strength of the polymer material that constitute the acetabular cup 10, chemical stability of the bond, and capability to form a large amount of a phosphorylcholine group on the bearing surface of the artificial joint replacement thereby increasing the density of the polymer layer 30.

A polymerizable monomer having a phosphorylcholine group is used for formation of a polymer layer 30. The polymer layer 30 can be grafted from the bearing surface of the acetabular cup 10 by selecting a monomer having a phosphorylcholine group in the side chain and a functional group capable of graft-polymerizing with a polymer constituting the acetabular cup 10 in the main chain.

Examples of the polymerizable monomer suited for use in the present invention include 2-methacryloyloxyethyl phosphorylcholine, 2-acryloyloxyethyl phosphorylcholine, 4-methacryloyloxybutyl phosphorylcholine, 6-methacryloyloxyhexyl phosphorylcholine, ω-methacryloyloxyethylene phosphorylcholine and 4-styryloyloxybutyl phosphorylcholine. Among these polymerizable monomers, MPC is particularly preferable.

An MPC monomer has a chemical structural formula shown below and includes a phosphorylcholine group and a polymerizable methacrylate unit. The MPC monomer has a feature that a high molecular weight MPC polymer can be easily prepared by radical polymerization (Ishihara et al.: Polymer Journal, Vol. 22, pp. 355 (1990). Therefore, when the polymer layer 30 is synthesized from the MPC monomer, grafting of the polymer layer 30 with the bearing surface can be conducted under comparatively mild conditions and also a large amount of graft polymers with a phosphorylcholine group can be formed on the bearing surface by forming the polymer layer 30 having high density.

[Chemical Formula 1]

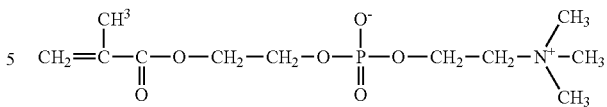

The polymer layer 30 that can be used in the present invention can also be formed from not only a homopolymer constituting a single polymerizable monomer having a phosphorylcholine group, but also a copolymer comprising a monomer having a phosphorylcholine group and the other vinyl compound. Thus, a function such as improved mechanical strength can be imparted to the polymer layer 30.

While the cup substrate 12 of the acetabular cup 10 is made of a polymer material having a methylene repeating unit, it is preferable to use UHMWPE. Among polymer materials having a methylene repeating unit, UHMWPE has particularly favorable mechanical properties such as wear resistance and deformation resistance, and is therefore suitable for the cup substrate 12. The higher the molecular weight of UHMWPE, the higher the wear resistance becomes. It is therefore preferable to use UHMWPE having a molecular weight of 1,000,000 g/mol or more, and more preferably molecular weight of 3,000,000 g/mol or more.

CLPE made by a crosslinking treatment of UHMWPE has even more favorable mechanical properties than UHMWPE, and is more preferably used to form the cup substarte 12 of the acetabular cup 10. The cup substrate 12 made of CLPE can be made by irradiating UHMWPE with high energy beams such as X-ray, electron beam or gamma-ray to apply a crosslinking treatment, and forming the material into a cup shape. While the crosslinking treatment can also be conducted by using a crosslinking agent instead of the high energy ray, it is not practical in case safety of the crosslinking agent is not ensured when applied to a material used in the human body such as artificial joint. The crosslinking treatment by means of the high energy beam, in contrast, can be done without compromising the safety of UHMWPE, and is preferably employed.

It is particularly preferable that the cup substrate 12 made of CLPE has free radicals generated when irradiated with high energy beam such as X-ray, electron beam or gamma-ray. Free radicals contained in the cup substrate 12 can act as an initiator for polymerization, during graft polymerization of a polymerizable monomer on the bearing surface of the cup substrate 12, and therefore helps increase the density of the polymer layer 30 of the covered bearing surface 16. However, reforming the cup substrate 12 as a whole into CLPE leads to an increase in the manufacturing cost. Therefore, it is also preferable to apply a crosslinking treatment only to the bearing surface of the cup substrate 12 to modify the surface region into CLPE, so as to use the cup substrate 12 having the covered bearing surface 16 of improved wear resistance in the acetabular cup 10.

The cup substrate 12 made of CLPE having such free radicals can be made by preparing the polymer material having a methylene repeating unit irradiated with high energy beam before the process of forming a cup substrate 12 in shape. Preparation of this polymer material involves a process of irradiating a polymer material having a methylene repeating unit with the high energy beam and a process of applying a heat treatment to the polymer material that has been irradiated with high energy ray at a temperature lower than a melting point thereof. By irradiating the cup substrate 12 made of UHMWPE with high energy beam to generate a large amount of free radicals and then applying a heat treatment at a temperature lower than the melting point, most of the free radicals can be consumed in the C-C recombination and crosslinking bond while leaving a part of the free radicals to remain within the cup substrate 12. It is not desirable to apply the heat treatment at a temperature higher than the melting point, which results in the consumption of substantially all of the free radicals.

The acetabular cup 10 for the artificial hip joint of this embodiment can be manufactured by forming the polymer material having a methylene repeating unit (for example, UHMWPE) into shape of the cup substrate 12 by machining, then grafting the polymer layer 30 having a phosphorylcholine group from the bearing surface of the cup substrate 12. To graft the polymer layer 30 having a phosphorylcholine group from the bearing surface of the cup substrate 12, a photoinduced polymerization initiator is applied to the bearing surface of the cup substrate 12, the cup substrate 12 is immersed in a solution that contains polymerizable monomer having a phosphorylcholine group and, in this state, is irradiated on the bearing surface with ultraviolet light (having wavelength of, for example, from 300 to 400 nm). As the bearing surface of the cup substrate 12 is irradiated with ultraviolet light, polymerizable monomer located near the bearing surface is polymerized so as to form the polymer layer 30, and the polymer layer 30 is grafted from the bearing surface.

The thickness of the polymer layer 30 obtained as described above depends on the concentration of the monomer in the solution containing the polymerizable monomer, solution temperature, ultraviolet-ray irradiation time and the amount of free radicals contained in the cup substrate 12. The polymer layer 30 having a desired thickness can be obtained by controlling these factors. The ultraviolet-ray irradiation time is preferably 40 minutes or more. In the polymer layer 30 that is formed under the conditions of example described in Japanese Patent Unexamined Publication (Kokai) No. 2003-310649 (concentration of solution is 0.5 mol/L and solution temperature is 60° C.), phosphoric index of the polymer layer 30 formed on the covered bearing surface 16 of the acetabular cup 10 increases at a high rate until the ultraviolet-ray irradiation time reaches 40 minutes. Accordingly, the ultraviolet-ray irradiation time is preferably set to 40 minutes or more.

To form the polymer layer 30 having a thickness of 10 to 200 nm by irradiating with ultraviolet light for 40 minutes, monomer concentration of the solution may be controlled within a range from 0.25 to 0.5 mol/L. When the monomer concentration is lower than 0.25 mol/L, not only the polymer layer 30 becomes too thin, but also density of the polymer layer 30 formed on the bearing surface of the acetabular cup 10 decreases. When the monomer concentration is higher than 0.5 mol/L, the monomers polymerize with each other while being suspended in the solution, before reaching the bearing surface of the acetabular cup 10. Occurrence of such polymerization causes the monomer concentration to decrease locally, thus making it impossible for the polymer layer 30 to grow in thickness, while thickness of the polymer layer 30 increases in other portion where the monomer is supplied sufficiently. As a result, the polymer layer 30 becomes uneven in thickness thus resulting in low durability. Therefore, the monomer concentration higher than 0.5 mol/L is not desirable.

Second Embodiment

Figure 3:
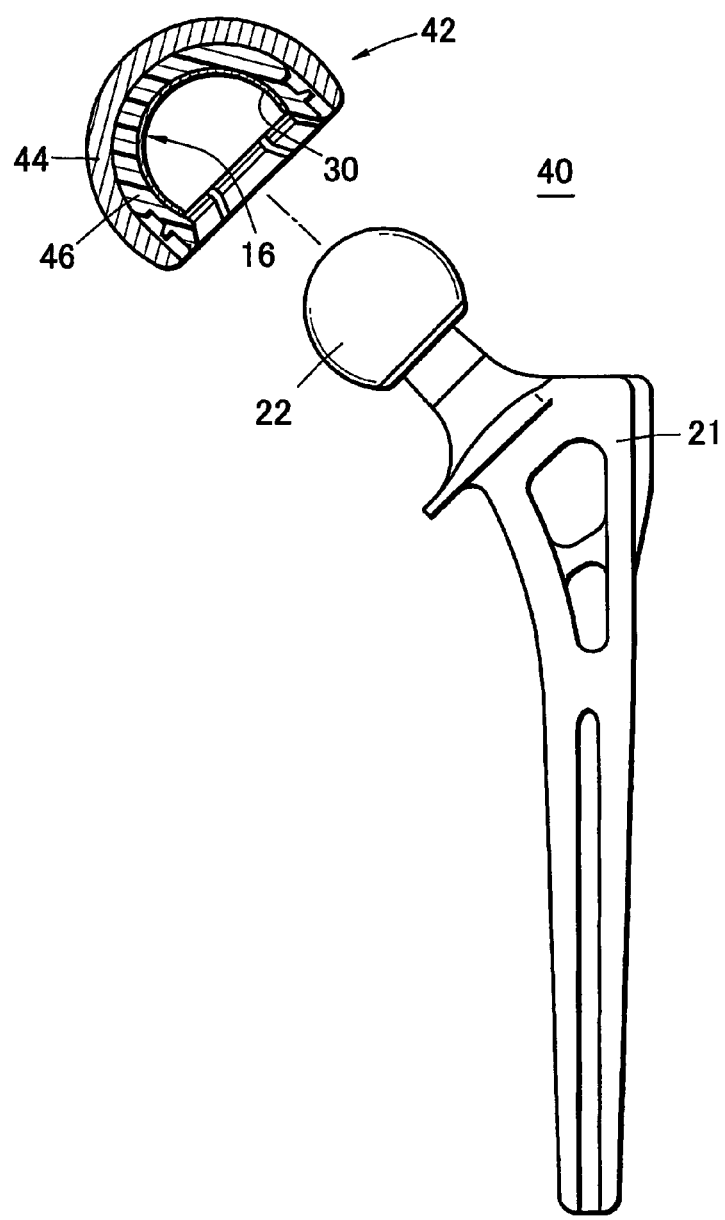
FIG. 3 is a schematic diagram of a bipolar artificial hip joint according to a second embodiment of the present invention.

FIG. 3 shows another artificial hip joint, a bipolar artificial hip joint 40. This artificial hip joint 40 is characterized by the constitution of the femoral head portion that comprises two components of a ball-shaped femoral head 22 and an outer head 42 that accommodates the femoral head 22.

The femoral head 22 consists of a ball-shaped component made of ceramics or a metal, and is fixed onto a stem body 21 at a proximate portion thereof.

The outer head 42 is constituted from an outer shell 44 that is a semi-spherical hollow component made of a metal or ceramics, a liner substrate 46 made of UHMWPE fixed onto the inside of the outer shell 44, and the polymer layer 30 fixed onto the spherical sliding surface that is formed in the liner substrate 46. The liner substrate 46 and the polymer layer 30 constitute the bearing materials of the artificial joint. The polymer layer 30 is made of polymer chains having a phosphorylcholine group grafted on the sliding surface, similarly to the case of the first embodiment.

The outer head 42 receives the femoral head 22 slidably to the covered sliding surface 16 of the liner substrate 46, thereby forming a first bearing section. The outer head 42 itself is also accommodated into the acetabulum of the patient's bone to form a second bearing section.

The bipolar artificial hip joint 40 is constituted so that the first bearing section and the second bearing section make sliding motions successively in accordance to the extent of movement of the hip joint. First, the first bearing section undergoes a first sliding motion and, when the movement of the hip joint goes beyond the movable range of the first bearing section, the second bearing section undergoes a second sliding motion. In the daily lives, the first sliding motion is predominant and the first bearing section is subject to more wear. In this embodiment, polymer layer 30 having a phosphorylcholine group is provided on the bearing surface of the liner substrate 46 of the outer head 42, so as to improve the tribological characteristic of the first (covered) bearing section, thereby achieving higher wear-resistance and higher durability. As a result, it is made possible to provide the artificial hip joint that suppresses wear debris from being generated and loosening from occurring over a long period of time, thereby reducing the number of revision surgeries required for the artificial joint or eliminating the need thereof altogether.

Third Embodiment

Figure 4:
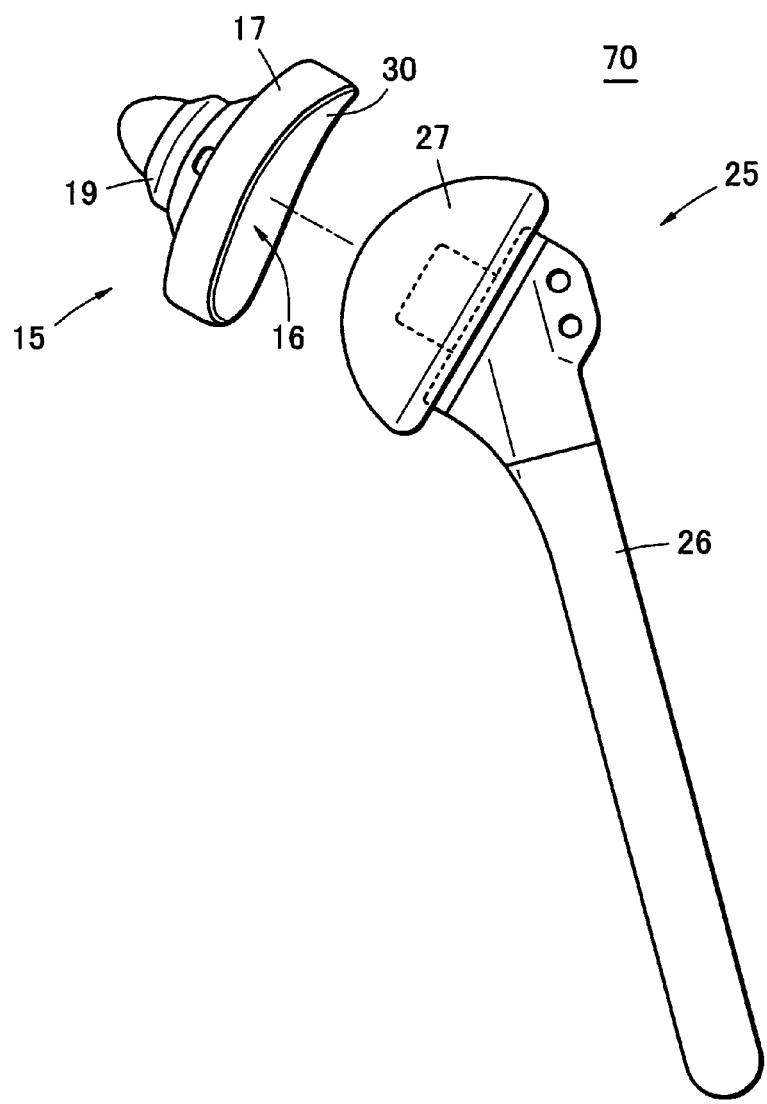
FIG. 4 is a schematic diagram of an artificial shoulder joint according to a third embodiment of the present invention.

FIG. 4 shows an artificial shoulder joint 70 that is constituted from a bearing component (glenoid cavity cup 15) that is fixed in the glenoid cavity of a shoulder blade and a humeral stem 25 that is fixed onto the humerus at the proximal end thereof.

The humeral stem 25 is constituted from a stem body 26 that is inserted into bone marrow of the humerus, and a humeral head 27 made of a metal or ceramics in substantially semi-spherical shape that is fixed onto proximal end of the stem body 26.

The glenoid cavity cup 15 comprises a cup substrate 17 that has a shoulder blade stem 19 embedded in the glenoid cavity of a shoulder blade and a bearing surface formed in a shallow concave shape, and the polymer layer 30 formed to coat the bearing surface. Similarly to the first embodiment, the polymer layer 30 is made of polymer chains having a phosphorylcholine group grafted from the bearing surface.

The artificial shoulder joint 70 functions as a shoulder joint that allows the arm to move back and forth and make swiveling motion, as the humeral head 27 of the humeral stem 25 is put into contact with the covered bearing surface 16 of the glenoid cavity cup 15 and is caused to make sliding motion.

In the artificial shoulder joint 70 of the third embodiment, polymer layer 30 having a phosphorylcholine group is provided on the bearing surface of the cup substrate 17, so as to improve the tribological characteristic of the bearing component, thereby achieving higher wear-resistance and higher durability. As a result, it is made possible to provide the artificial shoulder joint that suppresses wear debris from being generated and loosening from occurring over a long period of time, thereby reducing the number of revision surgeries required for the artificial joint or eliminating the need thereof altogether.

Fourth Embodiment

Figure 5:
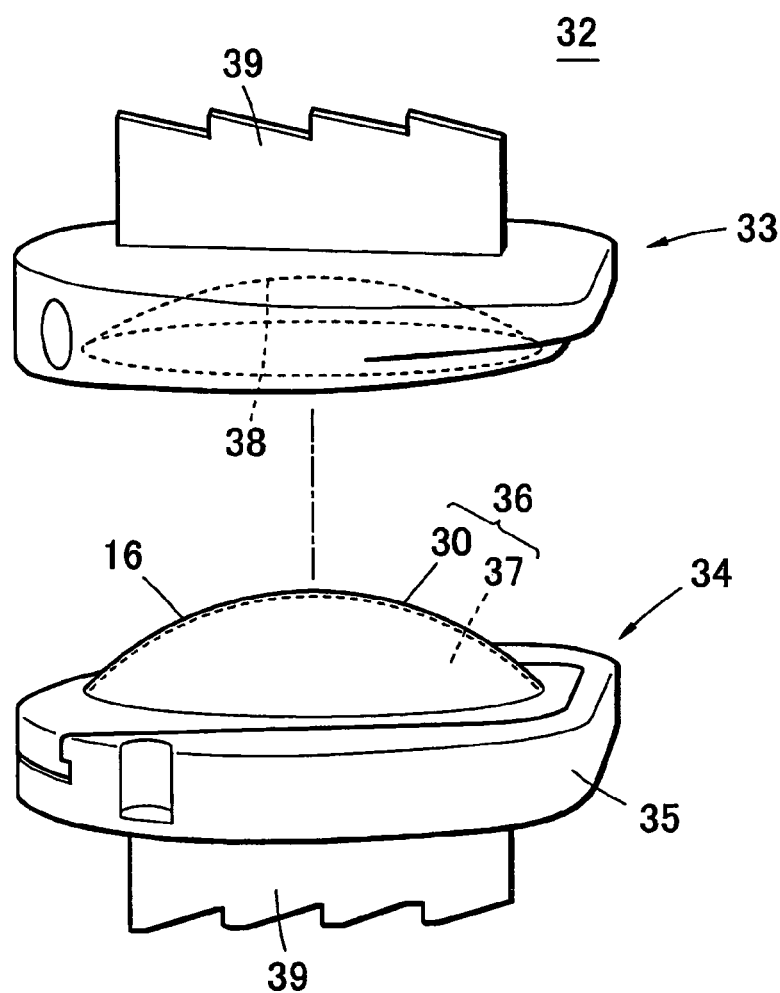
FIG. 5 is a schematic diagram of an artificial vertebral joint according to a fourth embodiment of the present invention.

FIG. 5 shows an artificial vertebral joint 32 that is constituted from an upper component 33 and a lower component 34 that are fixed between two bodies of vertebra which sandwich an intervertebral disk.

The lower component 34 is constituted from a convex sliding member 36 that ensures the sliding motion of the joint instead of the intervertebral disk, a metal casing 35 that accommodates the convex bearing component 36 and a stem 39 that protrudes from the bottom of the casing 35 and secures the lower component 34 onto the body of vertebra.

The convex bearing component 36 has a disk-shaped base body 37 having a swell (bearing surface) at the center thereof, and the polymer layer 30 with which the bearing surface is covered. Similarly to the first embodiment, the polymer layer 30 is made of polymer chains having a phosphorylcholine group grafted from the bearing surface.

The upper component 33 is made of a metal and has, on the bottom surface thereof, a concave receiving part 38 that slidably accommodates the covered bearing surface 16 of the convex bearing component 36 and, on the top surface thereof, the stem 39 that secures the upper component 33 onto the body of vertebra.

The artificial vertebral joint 32 constitutes a part of the spine that is capable of bending in all directions, by putting the concave receiving part 38 of the upper component 33 into contact with the covered bearing surface 16 of the convex bearing component 36 so as to make sliding motion.

In the artificial vertebral joint 32 of the fourth embodiment, the polymer layer 30 having a phosphorylcholine group is provided on the bearing surface of the convex bearing component 36 of the lower component 34, so as to improve the tribological characteristic of the bearing component, thereby achieving higher wear resistance and higher durability. As a result, it is made possible to provide the artificial vertebral joint that suppresses wear debris from being generated and loosening from occurring over a long period of time, thereby reducing the number of revision surgeries required for the artificial vertebral joint or eliminating the need thereof altogether.

Fifth to Eighth Embodiments

FIG. 6 to FIG. 9 show artificial joints for replacement of joints that govern movements of mainly bending back and forth. Such artificial joints can be classified into hinged type that links two constituent members of the joint by means of a shaft, and non-hinged type that uses two constituent members of the joint which do not contact with each other.

Hinged type artificial joints currently in use include artificial finger joints, artificial knee joints and artificial elbow joints, and unhinged type artificial joints include artificial knee joints, artificial elbow joints and artificial ankle joints.

Examples of unhinged type artificial joint and hinged type artificial joint will now be described.

Fifth Embodiment

Figure 6:
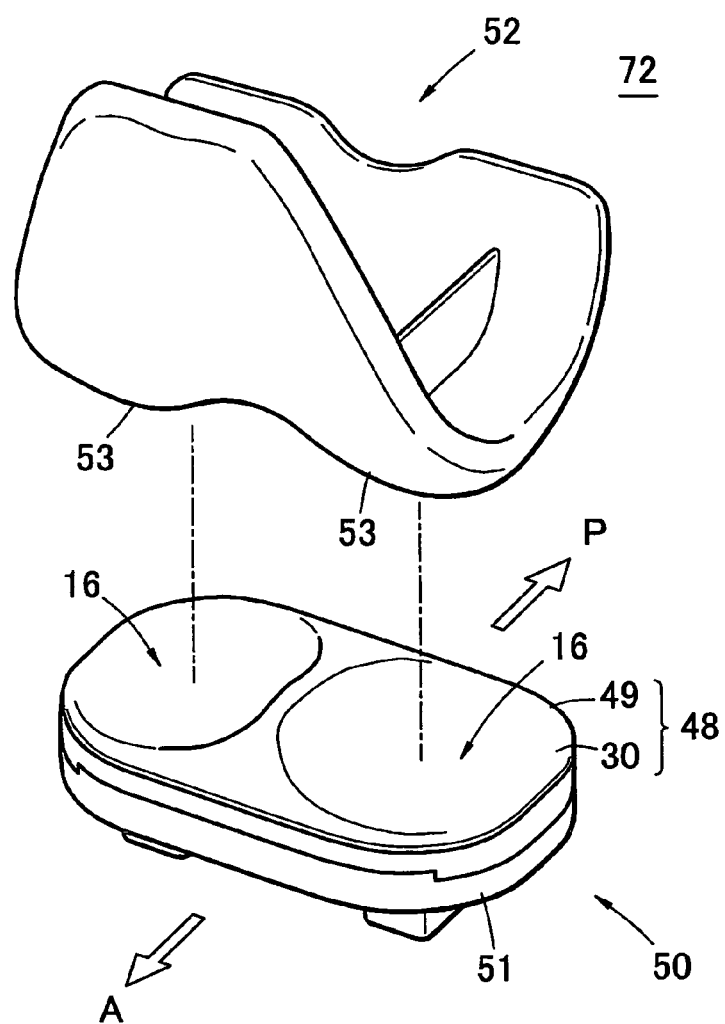
FIG. 6 is a schematic diagram of an artificial knee joint according to a fifth embodiment of the present invention.

FIG. 6 shows an artificial knee joint 72 of unhinged type that is constituted from a tibial component 50 that is fixed onto a proximal portion of a tibia and a joint replacement (femoral component 52) that is made of a metal or ceramics and is fixed onto a distal portion of a femur, with these components being fixed onto respective apophysial portions while being separated from each other.

The femoral component 52 has, on the bottom thereof, two curved protruding surfaces 53, 53 (inner condyle and outer condyle) that extend in an arc shape from the front (knee cap side indicated by arrow A) toward the back (back of knee indicated by arrow P).

The tibial component 50 of the artificial knee joint 72 is constituted from a bearing component (tibial tray 48) that forms the joint surface, and a tibial stem 51 that fixes the tibial tray 48 onto the tibia. The tibial tray 48 has curved recesses formed on the top surface thereof to extend from the front A toward the back P, the recesses serving as the covered bearing surfaces 16, 16 that make contact with two protruding surfaces 53, 53 of the femoral component 52. More specifically, the tibial tray 48 comprises a tray substrate 49 made of UHMWPE and the polymer layer 30 with which the bearing surfaces of the tray substrate 49 are covered. Similarly to the first embodiment, the polymer layer 30 is made of polymer chains having a phosphorylcholine group grafted from the bearing surface 16.

The artificial knee joint 72 of the fifth embodiment enables bending and extending motion in the anteroposterior direction by making sliding motion between the protruding surfaces 53, 53 of the femoral component 52 and the covered bearing surfaces 16, 16 of the tibial tray 48.

Sixth Embodiment

Figure 7:
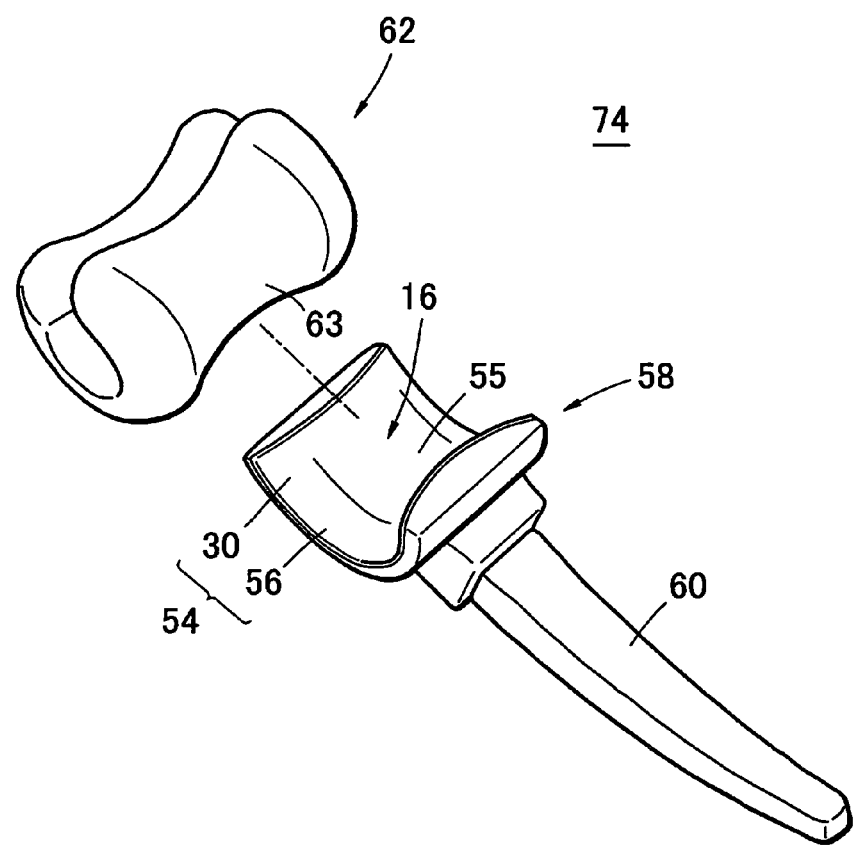
FIG. 7 is a schematic diagram of an artificial elbow joint according to a sixth embodiment of the present invention.

FIG. 7 shows an artificial elbow joint 74 of unhinged type, that is constituted from an ulnar component 58 to be fixed onto a proximal portion of ulna, and a joint replacement (humeral component 62) that is fixed onto a distal portion of the humerus, with these components being fixed onto respective apophysial portions while being separated from each other.

The ulnar component 58 is constituted from a sliding member (ulnar tray 54) that constitutes the joint surface and an ulnar stem 60 that fixes the ulnar tray 54 onto the ulna. The ulnar tray 54 has a shape of an annular component a part of which is cut off in the radial direction, with the inner surface thereof serving as the covered bearing surface 16. The bearing surface of the ulnar tray 54 forms a ridge 55 that rises from both edges toward the center in the direction of width and extends along the circumference.

More specifically, the ulnar tray 54 comprises a tray substrate 56 made of UHMWPE and the polymer layer 30 with which the bearing surfaces of the tray substrate 56 is graft-coated. Similarly to the first embodiment, the polymer layer 30 is made of polymer chains having a phosphorylcholine group grafted from the bearing surface.

The humeral component 62 of the artificial elbow joint 74 is made of a metal or ceramics and has a substantially cylindrical shape with a part thereof being cut off. Circumference of the humeral component 62 is slightly recessed at the center so as to form a shape of pulley 63.

The pulley 63 of the humeral component 62 and the ridge 55 of the ulnar tray 54 are engaged with each other, so as to form an artificial elbow joint that is capable of bending and extending in the anteroposterior direction.

Seventh Embodiment

Figure 8:
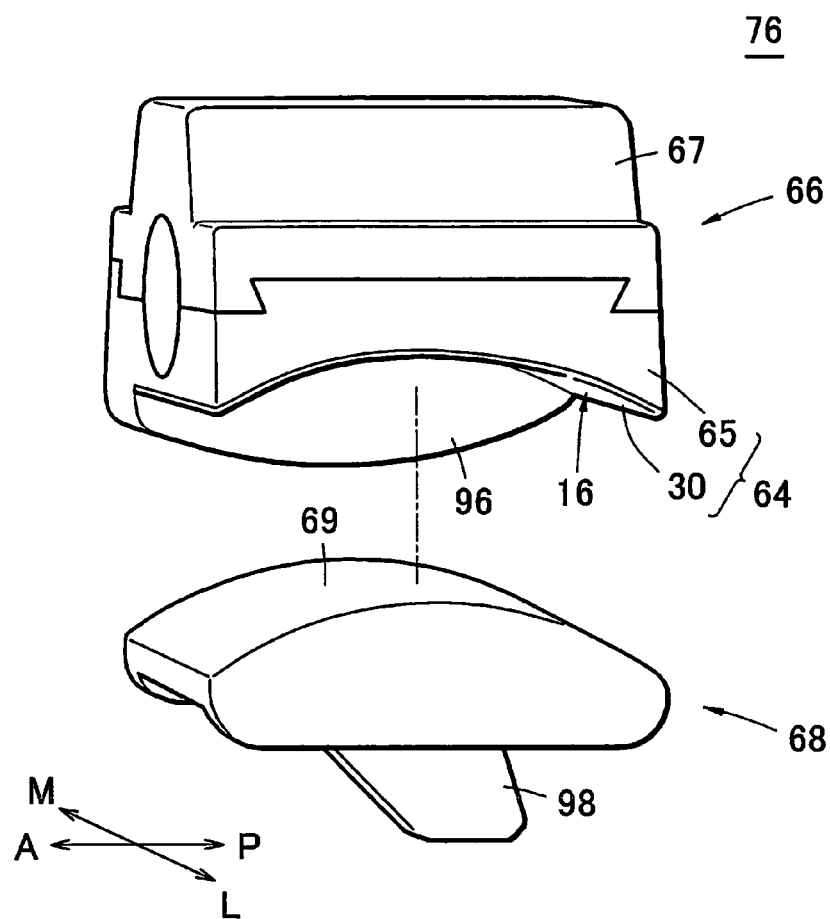
FIG. 8 is a schematic diagram of an artificial ankle joint according to a seventh embodiment of the present invention.

FIG. 8 shows an artificial ankle joint (for left foot) of unhinged type, that is constituted from a tibial component 68 fixed onto a distal portion of the tibia and a joint replacement (ankle bone component 68) that is fixed onto a proximal portion of the ankle bone, with these components being fixed onto respective apophysial portions while being separated from each other.

The tibial component 66 is constituted from a bearing component (tibial tray 64) that constitutes the joint surface and a tibial stem 67 that fixes the tibial tray 64 onto the tibia.

The tibial tray 64 has a bottom surface formed into concave surface that warps from the front A toward the back P, the bottom surface serving as the covered bearing surface 16. A flange 96 protrudes from the edge of inside M of the tibial tray 64 downward, so as to prevent the joint from displacing laterally into dislocation. More specifically, the tibial tray 64 comprises a tray substrate 65 made of UHMWPE and the polymer layer 30 with which the bearing surfaces of the tray substrate 65 is graft-coated. Similarly to the first embodiment, the polymer layer 30 is made of polymer chains having a phosphorylcholine group grafted from the bearing surface.

The ankle bone component 68 of the artificial foot joint 76 is made of a metal or ceramics and has a top surface formed in convex surface that warps from the front A toward the back P. The ankle bone component 68 is fixed onto a proximal portion of the ankle bone by inserting the ankle bone stem 98 formed on the bottom surface into the bone marrow of the ankle bone.

The artificial foot joint that is capable of bending and extending in the anteroposterior direction is formed by putting the top surface of the ankle bone component 68 and the covered bearing surface 16 of the tibial tray 64 into slidable contact with each other.

In the fifth to seventh embodiments, the polymer layer 30 having a phosphorylcholine group is provided on the bearing surface of the tray substrate so as to improve the tribological characteristic of the bearing component, thereby achieving higher wear-resistance and higher durability. As a result, it is made possible to provide the artificial joint that suppresses wear debris from being generated and loosening from occurring over a long period of time, thereby reducing the number of revision surgeries required for the artificial joint or eliminating the need thereof altogether.

Eighth Embodiment

Figure 9:
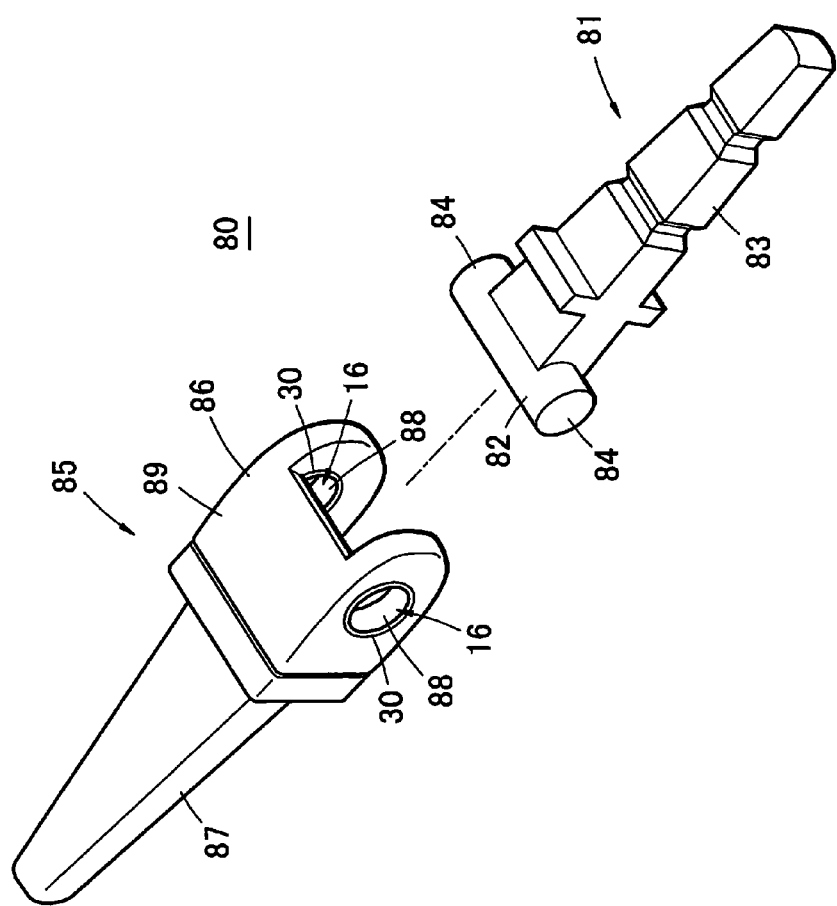
FIG. 9 is a schematic diagram of an artificial finger joint according to an eighth embodiment of the present invention.

FIG. 9 shows artificial finger joint 80 of hinged type used in arthroplasty for a joint between os metacarpale and finger bone or a joint between finger bones. The artificial finger joint 80 is constituted from a shaft component 81 fixed onto apophysial portion of the finger bone located at the distal side of the joint, and a receptor component 85 fixed onto apophysial portion of the finger bone located at the proximal side of the joint.

The shaft component 81 is integrally made of a metal or ceramics, and has a shaft part 82 that protrudes on both ends 84, 84 and a stem 83 that extends from the center of the shaft part 82 for fixing the shaft part 82 onto apophysial portion.

A bearing component 85 of the artificial finger joint 80 comprises a bearing component 86 having two bearing holes 88, 88 where the ends of the shaft part are to be fitted in, and a stem 87 for fixing the bearing component 86 onto apophysial portion. More specifically, the bearing component 86 comprises a bearing substrate 89 made of UHMWPE and the polymer layer 30 with which the covered bearing surfaces 16 of the bearing holes 88 is covered. Similarly to the first embodiment, the polymer layer 30 is made of polymer chains having a phosphorylcholine group grafted from the bearing surface.

In the artificial finger joint 80, a hinge structure is formed by fitting the ends 84 of the shaft part 82 into the bearing holes 88 of the bearing component 85. In the hinge structure, the shaft part 82 rotates in the bearing holes 88 so that the artificial finger joint 80 can bend and extend.

In the eighth embodiment, the polymer layer 30 having a phosphorylcholine group is provided on the bearing surface of the bearing holes 88 so as to improve the tribological characteristic of the hinge structure, thereby achieving higher wear-resistance and higher durability. As a result, it is made possible to provide the artificial finger joint that suppresses wear debris from being generated and loosening from occurring over a long period of time, thereby reducing the number of revision surgeries required for the artificial finger joint or eliminating the need thereof altogether.

EXAMPLE 1

As a model for artificial joint, the acetabular cup 10 for the artificial hip joint shown in FIG. 1 and FIG. 2 was made, and hydrophilicity, phosphoric index and durability (period over which wear resistance can be maintained) were evaluated. The cup substrate 12 of the acetabular cup 10 was made of CLPE, and samples a to g were made.

Conditions under which samples b to g graft-coated with the polymer layer 30 were made are described below. Sample a was made without the polymer layer 30 formed thereon for the purpose of comparison.

Preparation of Sample b

Sample b was made by the following process.

Step 1: A cup substrate 12 of the acetabular cup 10 immersed in an acetone solution of benzophenone (concentration of 10 mg/mL) for 30 seconds was pulled out of the solution and the solvent was removed from the surface of the cup substrate 12.

Step 2: With the cup substrate 12 being immersed in a aqueous solution of MPC (monomer concentration of 0.5 mol/L and solution temperature of 60° C.), the bearing surface of the cup substrate 12 was irradiated with ultraviolet light (wavelength of 300 to 400 nm) for 25 minutes thereby forming a polymer layer (MPC polymer) 30 grafted from the bearing surface.

Step 3: The cup substrate 12 was taken out of the MPC solution and was sufficiently washed with pure water.

Preparation of Sample c

Sample c was made in the same manner as in sample b, except for changing the ultraviolet-ray irradiation time to 50 minutes in the step 2.

Preparation of Sample d

Sample d was made in the same manner as in sample b, except for changing the ultraviolet-ray irradiation time to 90 minutes in the step 2.

Preparation of Sample e

Sample e was made in the same manner as in sample b, except for changing the ultraviolet-ray irradiation time to 180 minutes in the step 2.

Preparation of Sample f

Sample f was made in the same manner as in sample d, except for changing the monomer concentration in the MPC solution to 0.25 mol/L.

Preparation of Sample g

Sample g was made in the same manner as in sample d, except for changing the monomer concentration in the MPC solution to 1.00 mol/L and ultraviolet-ray irradiation time in the step 2 to 90 minutes.

Measurements of Hydrophilicity and Phosphoric Index

A static-water contact angle (indication of hydrophilicity) and a phosphoric index were measured on the MPC polymer layer 30 of each sample, with the results shown in Table 1.

TABLE 1

| Sample No. | Monomer concentration (mol/L) | Ultraviolet-ray irradiation time (minutes) | static-water contact angle (degrees) | Phosphoric index |
|---|---|---|---|---|
| Sample a | 0 | 0 | 89 | 0 |
| Sample b | 0.50 | 25 | 51 | 0.1 |
| Sample c | 0.50 | 50 | 14 | 0.32 |
| Sample d | 0.50 | 90 | 14 | 0.46 |
| Sample e | 0.50 | 180 | 14 | 0.48 |
| Sample f | 0.25 | 90 | 20 | 0.45 |
| Sample g | 1.00 | 90 | 48 | 0.35 |

Accelerated Joint Simulator Wear Test

An accelerated joint simulator wear test was conducted in an environment mimicking the operating conditions in the human body, by forcibly sliding the acetabular cup of sample a to g and the artificial femoral head with each other.

Figure 10:
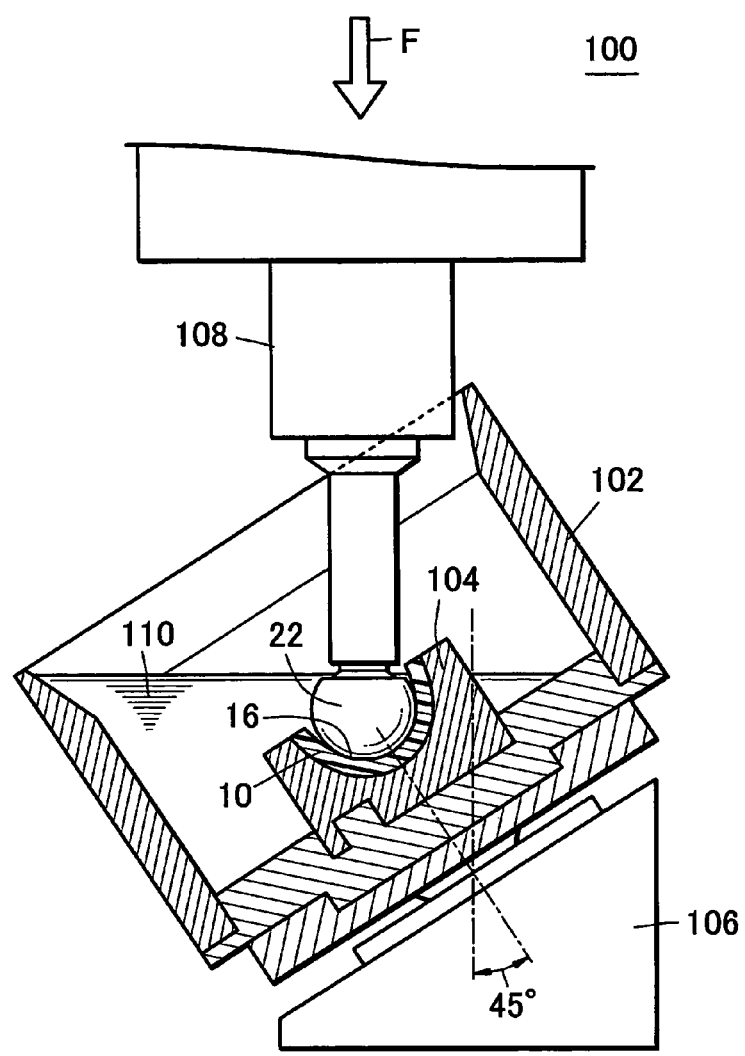
FIG. 10 is a schematic diagram of a joint simulator wear test apparatus used in Examples of the present invention.

The accelerated joint simulator wear test employed a wear test apparatus manufactured by MTS Corp. capable of simulating the state of sliding while the hip joint is swiveling. FIG. 10 is a schematic side view of the wear test apparatus 100 that has a container 102 which stores a body fluid-like lubricant and is connected in a slanted state (for example, at an angle of 45°) to a motor 106. The container 102 has, on the bottom thereof, a holder 104 that holds the acetabular cup 10. There is a femoral head mounting spindle 108 having the femoral head mounted on the distal end thereof disposed above the container 102, so as to be capable of applying a load F downward on the femoral head 22 that is fitted into the covered bearing surface 16 of the acetabular cup 10.

In the accelerated joint simulator wear test, in order to evaluate the durability of the acetabular cup 10 in an environment mimicking the operating conditions in the human body, the acetabular cup 10 and the femoral head 22 were immersed in 25% bovine serum 110 containing 0.1% sodium azide and 20 mM trisodium ethylenediaminetetraacetate. The femoral head 22 was made of a commercially available cobalt chromium alloy (26 mm in diameter). The test simulated the state of walking under Double Peak Paul conditions involving two peaks of 183 kg and 280 kg in one walking cycle per second. The bovine serum 110 was renewed every 500,000 cycles.

In the accelerated joint simulator wear test conducted under the conditions described above, sample was weighed at intervals of 500,000 cycles, and the initial sample weight measured before the wear test was divided by this weight to determine the gravimetric wear. The results are shown in FIG. 11 and FIG. 12, where graphs a to g show the test results of samples a to g, respectively.

Figure 11:
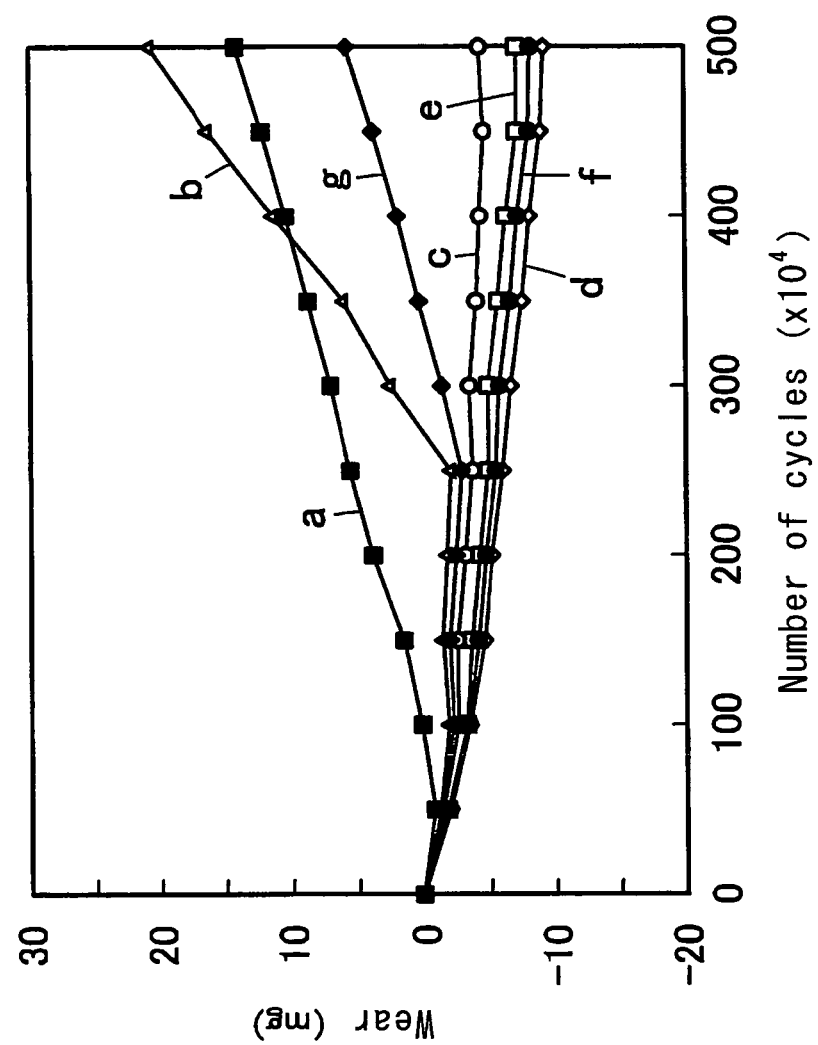
FIG. 11 is a graph showing the result of a joint simulator wear test conducted on the acetabular cup according to Example 1 of the present invention.
Figure 12:
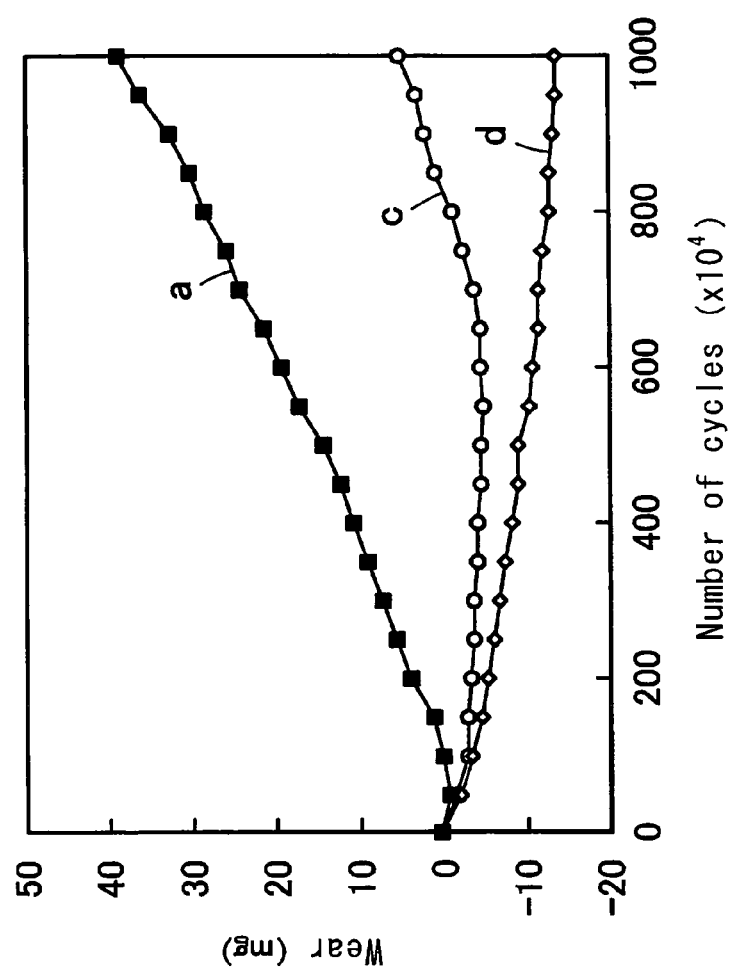
FIG. 12 is a graph showing the result of a joint simulator wear test conducted on the acetabular cup according to Example 1 of the present invention.

The graphs shown in FIG. 11 and FIG. 12 include negative values for the weight change. This means a weight increase resulting from absorption of water by the MPC polymer layer 30 and the cup substrate 12 that constitute the sample. In this example, a negative value of weight change (an increase in weight) is interpreted to represent zero wear.

FIG. 11 shows the test results of up to 5,000,000 cycles. Samples b to g that were graft-coated with the MPC polymer layer showed no significant increase in wear until about 2,500,000 cycles, thus exhibiting satisfactory wear resistance. As the test continued beyond 3,000,000 cycles, however, wear on sample b increased suddenly, eventually reaching a level comparable to that of sample a (no MPC polymer layer provided) around 4,000,000 cycles and exceeding the wear of sample a beyond 4,500,000 cycles. Wear on sample g showed sudden increase beyond 3,500,000 cycles, a longer period than in the case of sample b, and thereafter showed wear at a rate comparable to that of sample a.

These results show that the acetabular cup having the MPC polymer layer on the bearing surface exhibits satisfactory wear resistance regardless of the density of the MPC polymer layer for a few years of use, although MPC polymer layer having low density loses the high wear-resistance altogether during an extended period of use. Somewhat lower durability of sample g despite high phosphoric index is supposedly because thickness of sample g was large thus resulting in a conflicting situation of locally unsatisfactory coating and high value of a phosphoric index.

FIG. 12 shows the test results of up to 10,000,000 cycles on samples a, c and d. Sample a (no MPC polymer layer provided) showed wear increasing at a rate roughly proportional to the number of cycles. Sample c showed extremely low wear until about 8,000,000 cycles, thus exhibiting excellent wear-resistance. Sample d showed no significant increase in wear until about 10,000,000 cycles, thus exhibiting excellent durability resistance and the ability to maintain wear resistance comparable to that at the start of use over a long period of time.

Among the results of accelerated joint simulator wear test shown in FIG. 11 and FIG. 12, those of samples prepared by using solution of the same monomer concentration are grouped, and sorted by three parameters of (1) an ultraviolet-ray irradiation time, (2) a static-water contact angle and (3) a phosphoric index. Resultant data are shown in FIGS. 13 to 15, where points a to e represent the test results of samples a to e, respectively.

Figure 13:
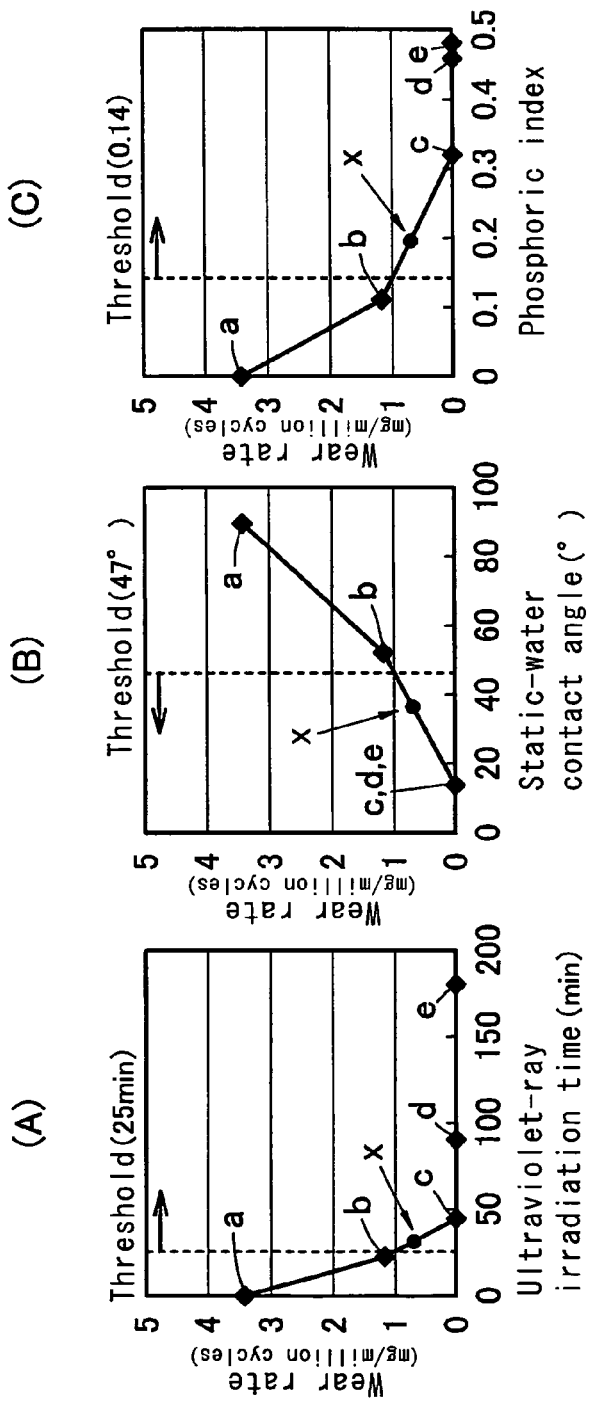
FIG. 13 (A to C) is a graph showing the results of a joint simulator wear test conducted on the acetabular cup according to Example 1 of the present invention.
Figure 14:
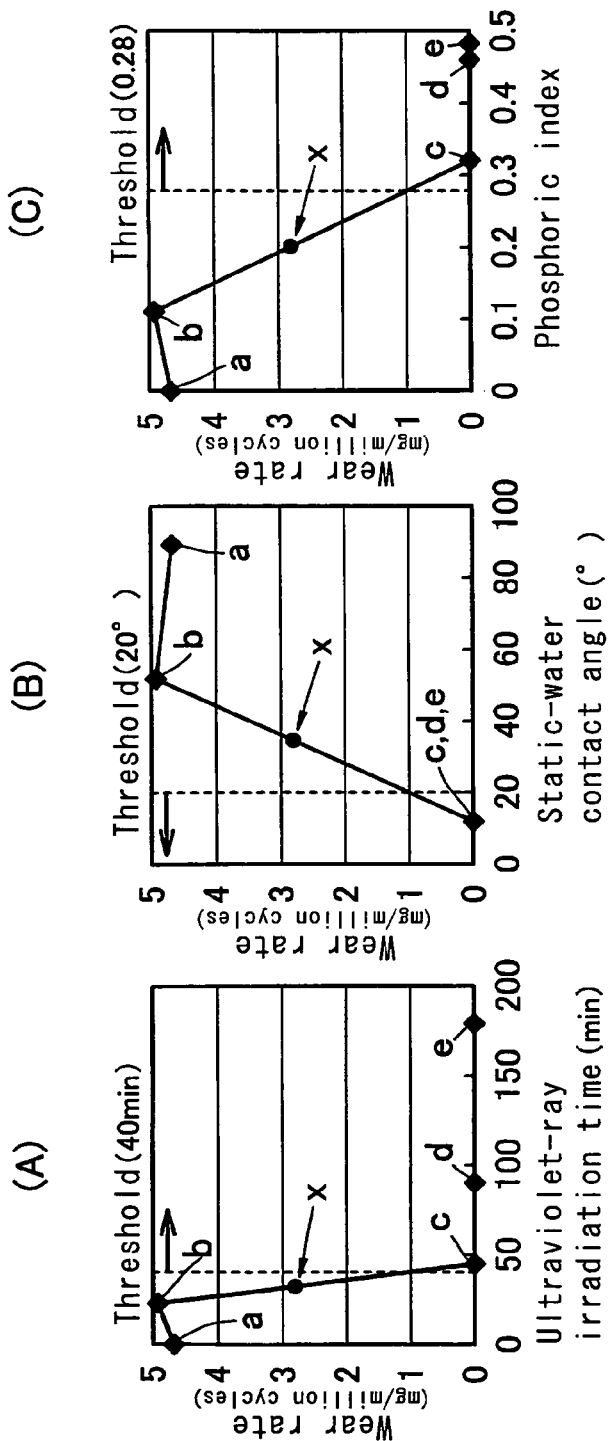
FIG. 14 (A to C) is a graph showing the results of a joint simulator wear test conducted on the acetabular cup according to Example 1 of the present invention.
Figure 15:
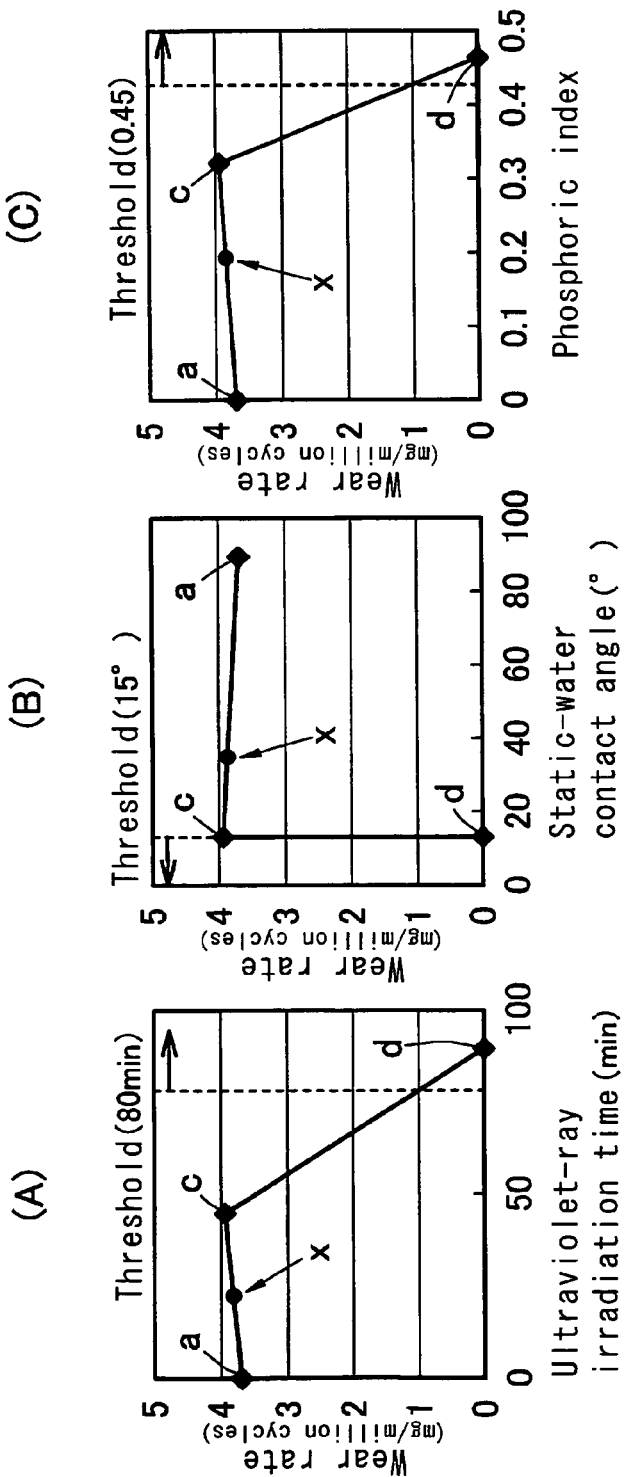
FIG. 15 (A to C) is a graph showing the results of a joint simulator wear test conducted on the acetabular cup according to Example 1 of the present invention.

In the graphs of FIGS. 13 to 15, wear rate (mg/1,000,000 cycles) plotted along the ordinate means the weight loss (mg) of the acetabular cup caused by wear during a period of 1,000,000 cycles. For example, wear rate at 10,000,000 cycles means the weight loss of the acetabular cup caused by wear during a period from 9,000,000 cycles to 10,000,000 cycles. 1,000,000 cycles in the accelerated joint simulator wear test is equivalent to one year of use, and therefore the wear rate gives the amount of wear debris that is expected to be generated in one year.

Normally, a small amount of wear debris is disposed of by macrophages. However, the amount of wear debris experienced in clinical applications is in the order of several hundreds of thousands to several thousands of thousands of particles, which far exceeds the physiological disposal capability of phagocytes. Cytokines (PGE2, TNF-α, IL-1, IL-6, etc.) released by phagocytes that have taken in such a large amount of wear dust are believed to stimulate osteoclasts thus resulting in osteolysis. In other words, osteolysis would be effectively suppressed from occurring by suppressing the amount of wear dust generated in a given period of time below the permissible limit of the amount of wear debris disposed in vivo. Thus the wear rate is considered to be a useful indicator of the effect of suppressing osteolysis.

In the conventional artificial hip joint, the acetabular cup made of UHMWPE shows wear rate of 10 to 20 mg/1,000,000 cycles, and the acetabular cup made of CLPE shows wear rate of 3 to 5 mg/1,000,000 cycles. In this example, upper limit of wear rate is set at 1 mg/1,000,000 cycles in order to clarify the range where the wear rate can be kept at a very low level. Experiments were conducted to find out the dependency of wear rate at a given number of cycles on the three parameters (ultraviolet-ray irradiation time, static-water contact angle and phosphoric index).

The graph of FIG. 13 shows the wear rate of the cup after undergoing 2,500,000 cycles of sliding motion (equivalent to about 3 years of use). In FIG. 13(A), wear rate is plotted against the ultraviolet-ray irradiation time (polymerization time). In FIG. 13(B), wear rate is plotted against the static-water contact angle. In FIG. 13(C), wear rate is plotted against the phosphoric index.

From these graphs, it can be concluded that the acetabular cup 10 can maintain satisfactory wear resistance after about three years of use when the bearing surface is graft-coated with MPC polymer layer that is treated with ultraviolet-ray irradiation for 25 minutes or more and the covered bearing surface 16 has static-water contact angle of 50° or less and phosphoric index of 0.15 or higher. When subjected to 2,500,000 cycles of test, wear rate of the acetabular cup 10 showed a trend of monotonous increase or decrease with respect to the three parameters of ultraviolet-ray irradiation time, static-water contact angle and phosphoric index.

The graph of FIG. 14 shows the wear rate of the cup after undergoing 5,000,000 cycles of sliding motion (equivalent to about 5 years of use). In FIG. 14(A), wear rate is plotted against the ultraviolet-ray irradiation time (polymerization time). In FIG. 14(B), wear rate is plotted against the static-water contact angle. In FIG. 14(C), wear rate is plotted against the phosphoric index.

From these graphs, it can be concluded that the acetabular cup 10 can maintain satisfactory wear resistance after about five years of use when the bearing surface is graft-coated with MPC polymer layer formed by ultraviolet-ray irradiation for a period of 40 minutes or more and the covered bearing surface 16 has a contact angle of 20° or less with water and a phosphoric index of 0.28 or more.

When subjected to 5,000,000 cycles of test, unlike the result with 2,500,000 cycles of test, wear rate of sample b (with MPC polymer layer having phosphoric index of 0.1) exceeded the wear rate of sample a (without MPC polymer layer).

The graph of FIG. 15 shows the wear rate of the cup after undergoing 10,000,000 cycles of sliding motion (equivalent to about 10 years of use). In FIG. 15(A), wear rate is plotted against the ultraviolet-ray irradiation time (polymerization time). In FIG. 15(B), wear rate is plotted against the static-water contact angle. In FIG. 15(C), wear rate is plotted against the phosphoric index.

From these graphs, it can be concluded that the acetabular cup 10 can maintain satisfactory wear resistance after about ten years of use when the bearing surface is graft-coated with MPC polymer layer that is formed with ultraviolet-ray irradiation for a period of 90 minutes or more and the covered bearing surface 16 has static-water contact angle of 14° or less and a phosphoric index of 0.45 or more.

When subjected to 10,000,000 cycles of test, wear rate of sample c (with MPC polymer layer having phosphoric index of 0.32) decreased to a level comparable to the wear rate of sample a (without MPC polymer layer).

From the results shown in FIG. 13 and FIG. 14, it is found that the acetabular cup having the MPC polymer layer formed thereon exhibits satisfactory wear resistance regardless of the density of the polymer layer for about three years of use, although MPC polymer layer having low density may not be capable of rendering sufficient durability to the acetabular cup after five years of use.

Comparison in terms of wear rate incurred in the accelerated joint simulator wear test (5,000,000 cycles) that is equivalent to about five years of use showed that wear rate of the acetabular cup (samples c to e) that employ the bearing material of the present invention was decreased to about 1/20 or less of the wear rate of the acetabular cup made of UHMWPE without MPC polymer layer, and to about 1/10 or less of the wear rate of the acetabular cup (sample a) made of CLPE without MPC polymer layer. Thus it has been proved that the bearing material of the present invention can endure clinical application over a long period of time.

COMPARATIVE EXAMPLE

Wear resistance of an acetabular cup (called sample X) made under the manufacturing conditions disclosed in Japanese Patent Unexamined Publication (Kokai) No. 2003-310649 was estimated and plotted as point X in FIGS. 13 to 15. Sample X was made in the same manner as in sample b, except for changing the ultraviolet-ray irradiation time to 30 minutes in the step 2.

Wear resistance of sample X remains within the permissible range up to 2,500,000 cycles but deviates beyond the permissible range as the use is elongated up to 5,000,000 cycles and decreases to a level of about the same level as that of sample a with no MPC polymer layer at 10,000,000 cycles.

Thus it has been made evident that it is not enough to form the polymer layer having a phosphorylcholine group on the bearing surface and it is necessary to increase the density of the polymer layer to be formed, for obtaining the bearing material that maintains high wear-resistance over a long period of time.

EXAMPLE 2

The atomic concentrations (atom %) of phosphorus atom and nitrogen atom of the covered bearing surface were measured on samples a to e made in this Example as the indirect indication of density of the MPC polymer layer provided on the bearing surface, to investigate the relationship between the atomic concentrations and durability of the sample.

As the chemical formula of the MPC monomer indicates, one molecule of the MPC monomer includes one phosphorus atom and one nitrogen atom. Therefore, proportions of phosphorus atoms and nitrogen atoms included in the measurement region (equivalent to atomic concentrations) are in proportion to the ratio of MPC molecules that exist in the region. This means that atomic concentrations of phosphorus atom and nitrogen atom can be used as the indicators of the density of the MPC polymer layer.

The atomic concentrations of phosphorus atom and nitrogen atom were determined by X-ray photoelectron spectroscopy (XPS). XPS measurement has far higher spatial resolution than the FT-IR employed in Example 1, and therefore has the advantage of the capability to measure even a sample surface that has irregularities. However, since XPS measurement covers only a small surface area, result of the measurement may greatly vary depending on the point of measurement, when the MPC polymer layer is not uniform. Accordingly, it is preferable to make XPS measurement at plurality of points and average the results.

XPS measurement was conducted by using Mg-K$\alpha$ line as the X-ray with an excitation voltage of 15 kV and take-off angle of 90°. The XPS spectrum thus obtained was used to determine the atomic concentration of phosphorus atom and atomic concentration of nitrogen atom. Atomic concentration will be given in terms of atom %.

XPS analysis of the MPC polymer layer formed on the bearing surfaces of samples a to e made in Example 1 gave the atomic concentration of phosphorus atom and atomic concentration of nitrogen atom in the MPC polymer layer as shown in Table 2.

TABLE 2

| Sample No. | Atomic concentration of phosphorus atom (atom %) | Atomic concentration of nitrogen atom (atom %) |
|---|---|---|
| Sample a | 0.00 | 0.0 |
| Sample b | 2.65 | 1.88 |
| Sample c | 5.29 | 4.10 |
| Sample d | 5.18 | 4.47 |
| Sample e | 5.54 | 4.59 |

Figure 16:
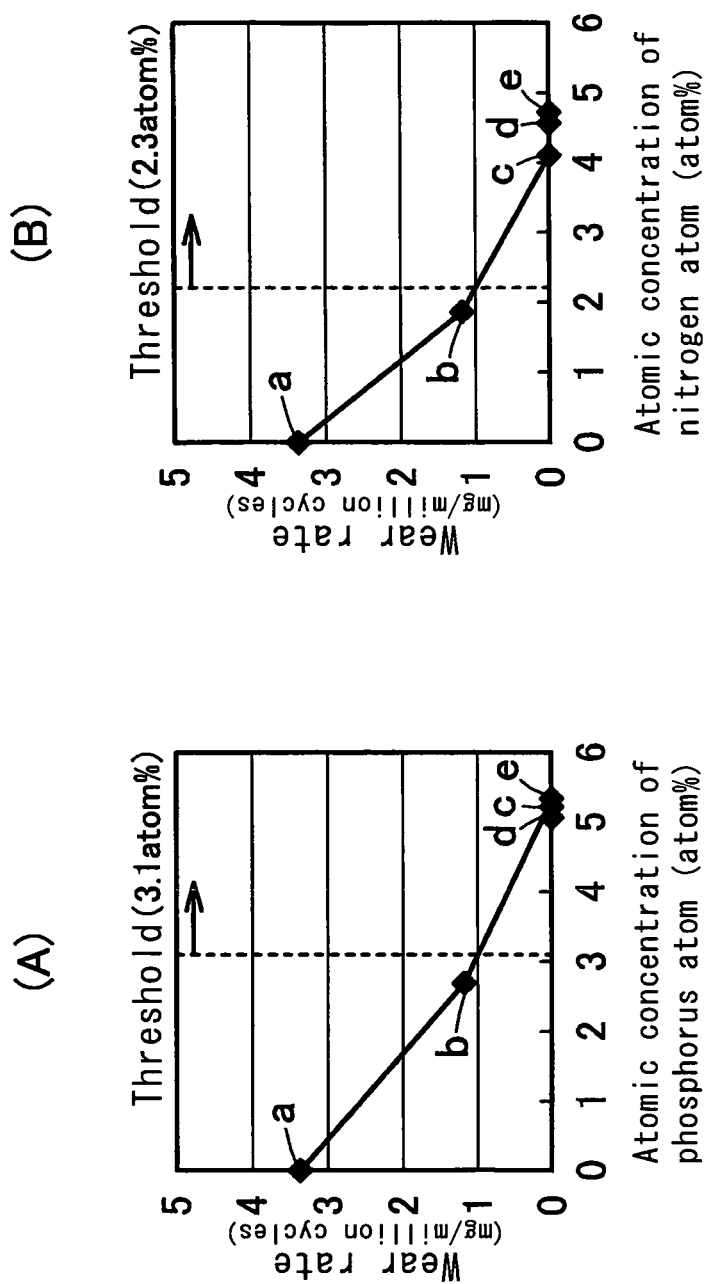
FIG. 16 (A, B) is a graph showing the results of a joint simulator wear test conducted on the acetabular cup according to Example 2 of the present invention.
Figure 17:
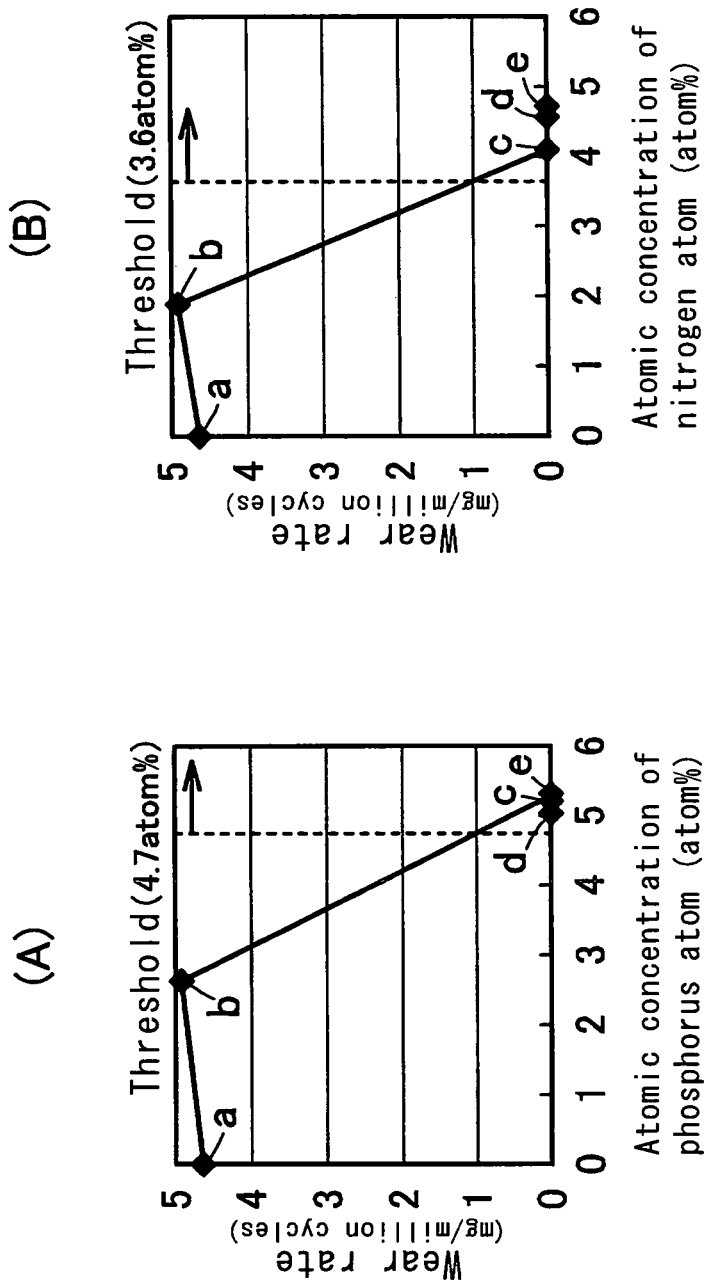
FIG. 17 (A, B) is a graph showing the results of a joint simulator wear test conducted on the acetabular cup according to Example 2 of the present invention.
Figure 18:
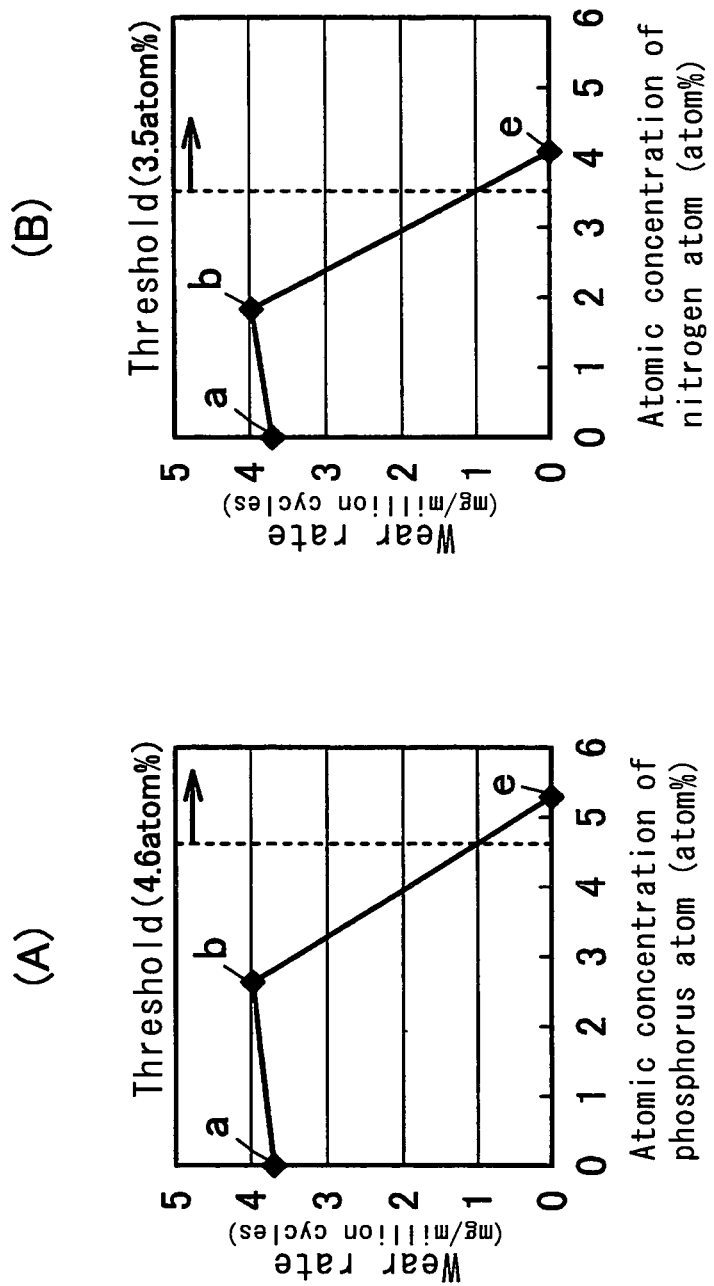
FIG. 18 (A, B) is a graph showing the results of a joint simulator wear test conducted on the acetabular cup according to Example 2 of the present invention.

Relationships between the atomic concentration and wear resistance (wear rate) derived from the results shown in Table 2 and the results of wear test of Example 1 are shown in FIGS. 16 to 18. Points a to e in the graph represent the test results of samples a to e, respectively.

The graph of FIG. 16 shows wear rate of the cup after 2,500,000 cycles of sliding motion (equivalent to about three years of use). The graph of FIG. 17 shows wear rate of the cup after 5,000,000 cycles of sliding motion (equivalent to about five years of use). The graph of FIG. 18 shows wear rate of the cup after 10,000,000 cycles of sliding motion (equivalent to about ten years of use). FIG. 16(A), FIG. 17(A) and FIG. 18(A) are graphs of wear rate plotted against the atomic concentration of phosphorus atom. FIG. 16(B), FIG. 17(B) and FIG. 18(B) are graphs of wear rate plotted against the atomic concentration of nitrogen atom.

Similarly to Example 1, upper limit of wear rate was set at 1 mg/1,000,000 cycles, and accordingly the threshold of operation cycles was determined.

From the graph of wear loss at 2,500,000 cycles shown in FIG. 16, it was found that satisfactory wear resistance can be maintained for a period of about three years when atomic concentration of phosphorus atom is 3.1 atom % or higher and atomic concentration of nitrogen atom is 2.3 atom % or higher. At 2,500,000 cycles, wear resistance showed a tendency of becoming higher as the atomic concentrations of both atoms increased.

From the graph of wear rate at 5,000,000 cycles shown in FIG. 17, it was found that satisfactory durability and satisfactory wear resistance for a period longer than about five years can be obtained when atomic concentration of phosphorus atom is 4.7 atom % or higher and atomic concentration of nitrogen atom is 3.6 atom % or higher. From the graph of wear rate at 10,000,000 cycles shown in FIG. 18, it was found that further higher durability and satisfactory wear resistance for an extended period over about five years can be obtained when atomic concentration of phosphorus atom is 4.6 atom % or higher and atomic concentration of nitrogen atom is 3.5 atom % or higher. In the test of 5,000,000 cycles, unlike the test of 2,500,000 cycles, sample b (having MPC polymer layer of atomic concentration of phosphorus atom 2.65 atom %, atomic concentration of nitrogen atom 1.86 atom %) showed wear rate larger than that of sample a (MPC polymer layer).

From the results shown in FIGS. 16 to 18, it is found that the acetabular cup having the MPC polymer layer formed thereon exhibits higher wear-resistance regardless of the density of the polymer layer for about three years of use, although MPC polymer layer having low density may not be capable of rendering sufficient durability to the acetabular cup after five years of use.

EXAMPLE 3

Thickness of the MPC polymer layer, with which the bearing surface of the acetabular cup is graft-coated, was measured on samples a, d, f and f made in Example 1. Sample was enclosed by epoxy resin, dyed with ruthenium tetrachloride and was cut into ultra-thin slice by using an ultra-microtome. The slice was observed under a transmission electron microscope (TEM) JEM-1010 of JEOL, Ltd. with acceleration voltage of 100 kV.

Figure 19A:
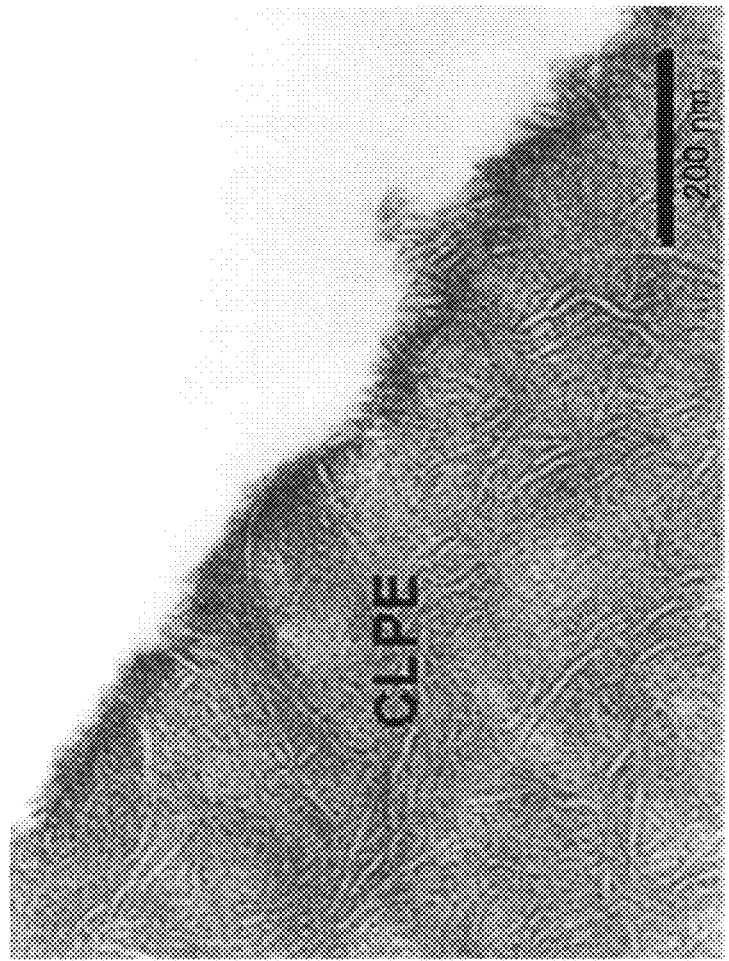
FIG. 19A is a cross-sectional TEM image of the acetabular cup according to Example 3 of the present invention.
Figure 19B:
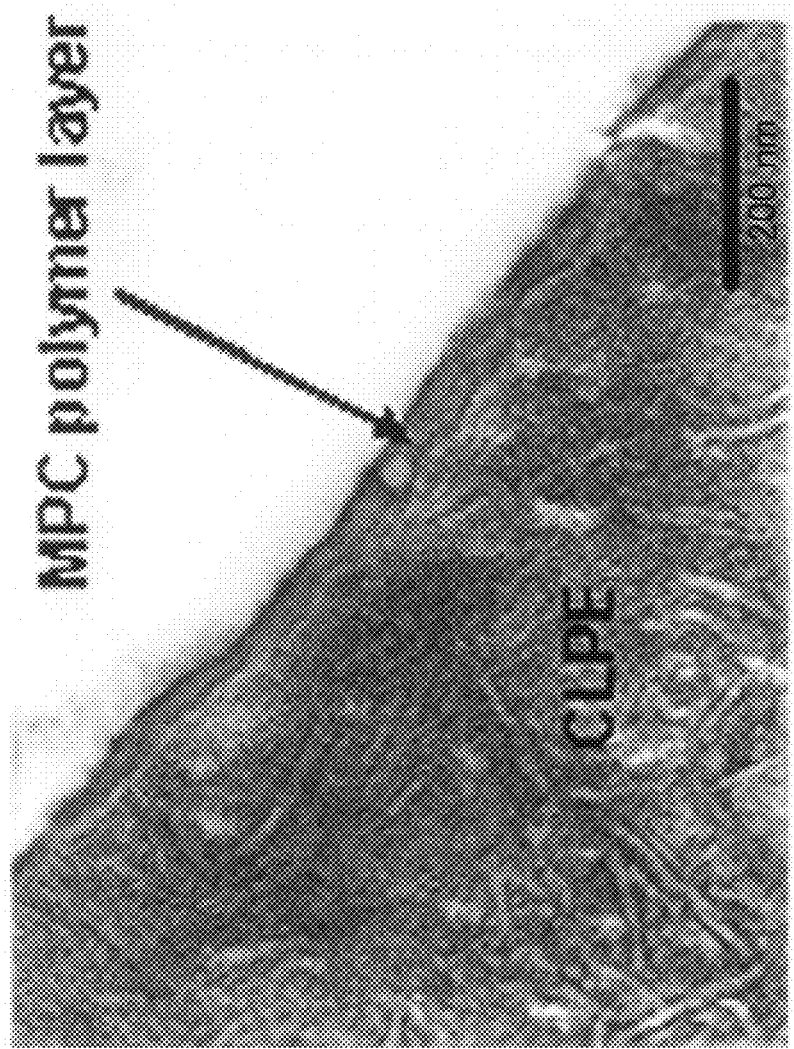
FIG. 19B is a cross-sectional TEM image of the acetabular cup according to Example 3 of the present invention.
Figure 19C:
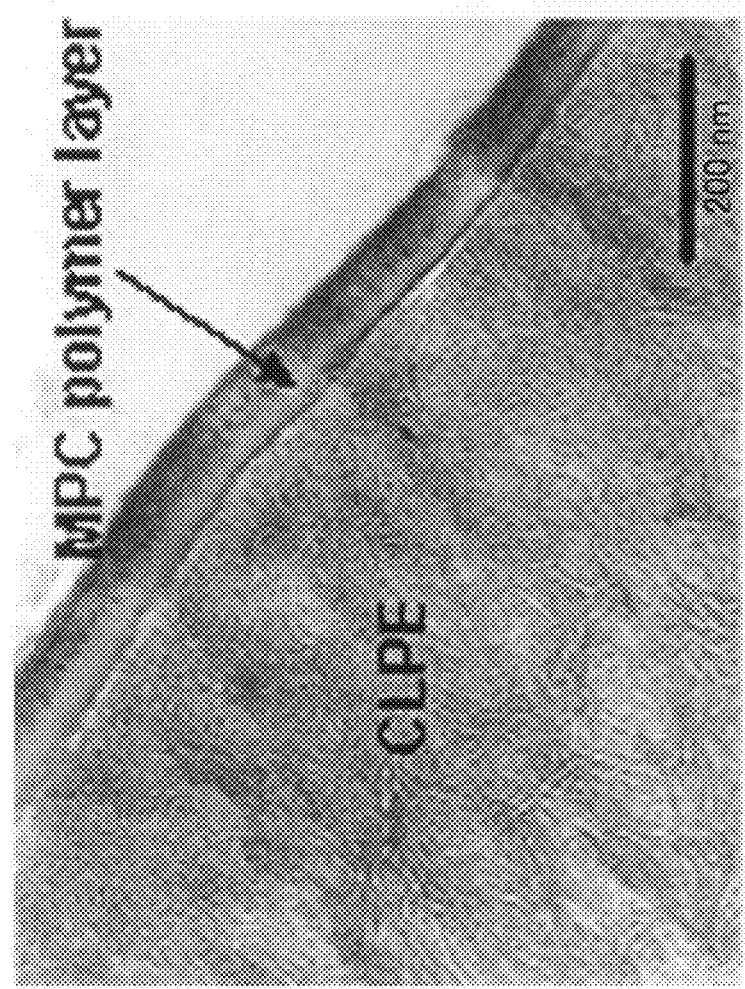
FIG. 19C is a cross-sectional TEM image of the acetabular cup according to Example 3 of the present invention.
Figure 19D:
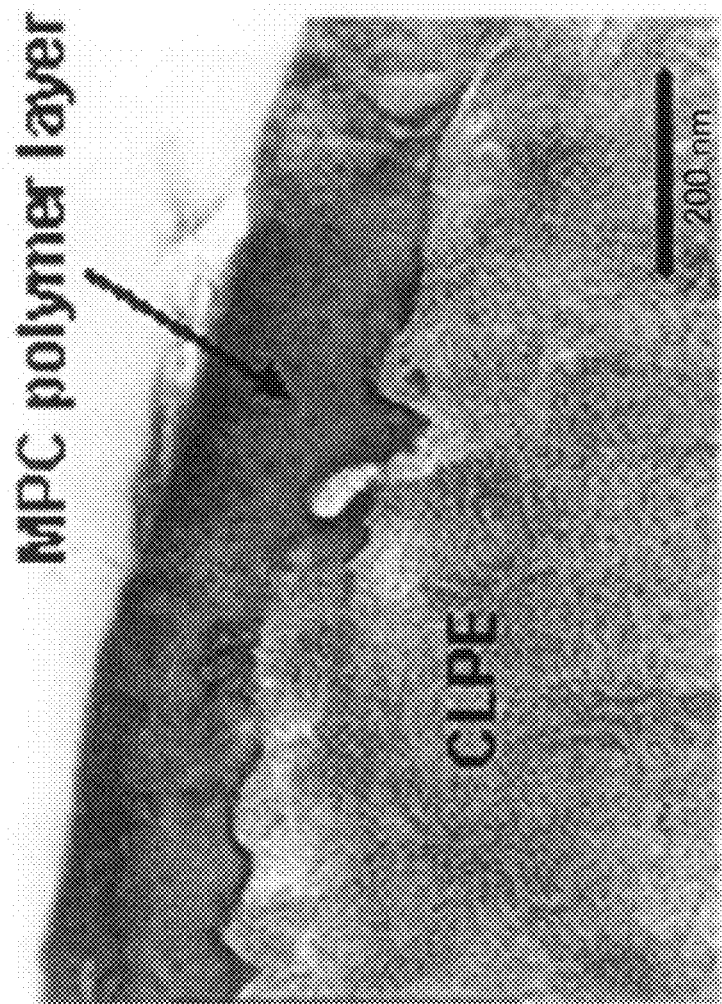
FIG. 19D is a cross-sectional TEM image of the acetabular cup according to Example 3 of the present invention.

FIG. 19A shows sample that was not covered with MPC polymer layer. FIG. 19B shows sample f (monomer concentration 0.25 mg/L). FIG. 19C shows sample d (monomer concentration 0.50 mg/L). FIG. 19D shows sample g (monomer concentration 1.00 mg/L).

FIGS. 19B to 19D showed a graft-coated layer (MPC polymer layer) not shown in FIG. 19A. In FIG. 19B, layer thickness is from 10 to 30 nm, and in FIG. 19C, layer thickness is from 100 to 200 nm. When TEM images were observed at various points, it was verified that the MPC polymer layer covered the entire bearing surface. In FIG. 19D, in contrast, MPC polymer layer with thickness from 200 to 250 nm is formed, although observation at various points showed that there are points where the layer is hardly formed, the so-called pin holes. These defects are supposedly caused by the following mechanism.

As the acetabular cup is immersed in a monomer solution and, in this state, the bearing surface is irradiated with ultraviolet light, benzophenone existing on the bearing surface is activated, and polyethylene existing on the bearing surface is then activated. An MPC monomer contained in the monomer solution reacts with the activated polyethylene and is grafted from the bearing surface. If the graft polymerization proceeds properly, density of the MPC polymer increases. Then MPC monomer contained in the monomer solution continues to polymerize with the MPC polymer grafted from the bearing surface so that the MPC polymer chain becomes longer, thus resulting in the growth of the film thickness. When the monomer concentration in the monomer solution is in a range from 0.25 mg/L (sample f) to 0.50 mg/L (sample d), graft polymerization proceeds properly. When the monomer concentration in the monomer solution is as high as 1.0 mg/L, however, the MPC monomer irradiated with ultraviolet light reacts with MPC monomer located nearby, before reaching the bearing surface, thus forming MPC polymer in the solution. This MPC polymer is not bonded with the bearing surface, and is therefore taken away from the acetabular cup when washed. Since the formation of this MPC polymer causes the MPC monomer concentration to decrease rapidly in the solution nearby, local regions of low monomer concentration are generated which, if the monomer concentration is too low, make it impossible to form the MPC polymer layer and result in pin holes.

As can be seen from the above discussion, uniform MPC polymer layer cannot be formed when the concentration of the MPC monomer solution is too low or too high, thus resulting in lower durability of the acetabular cup.

EXAMPLE 4

Figure 20:
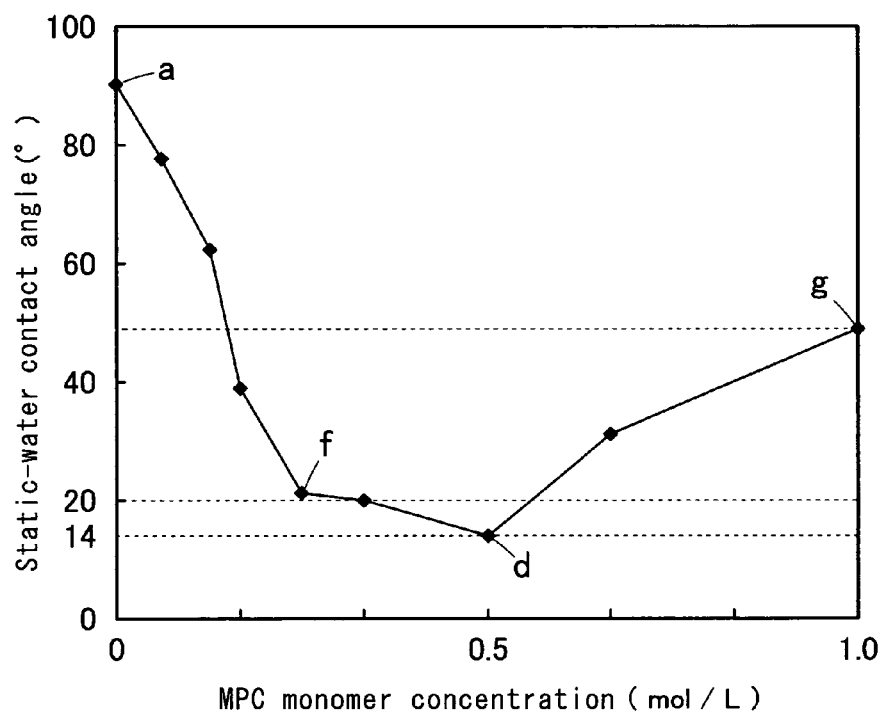
FIG. 20 is a graph showing the measurement results of a static-water contact angle of the acetabular cup surface according to Example 4 of the present invention.

Influence of varying only the monomer concentration on the properties of the MPC polymer layer was investigated under the conditions of making sample d in Example 1.
Measurement of Hydrophilicity A static-water contact angle (indicator of hydrophilicity) of the MPC polymer layer 30 was measured on a plurality of samples formed with various monomer concentrations, with the results shown in FIG. 20. Points a, d, f and g in the graph represent the test results of samples a, d, f and g, respectively, of Example 1. As can be seen from FIG. 20, contact angle showed the lowest (14°) when the monomer concentration was 0.50 mg/L, and remained at low levels of 20° or less when the monomer concentration was in a range from 0.25 mg/L to 0.50 mg/L. When the monomer concentration deviates from this range, the contact angle increases.

When the monomer concentration is too low, the contact angle is considered to increase due to low density of MPC polymer layer and thin polymer layer. When the monomer concentration is too high, MPC polymer layer becomes thicker but pin holes are more likely to be produced at points where the MPC polymer layer has lower density, thus resulting in higher contact angle.

Figure 21:
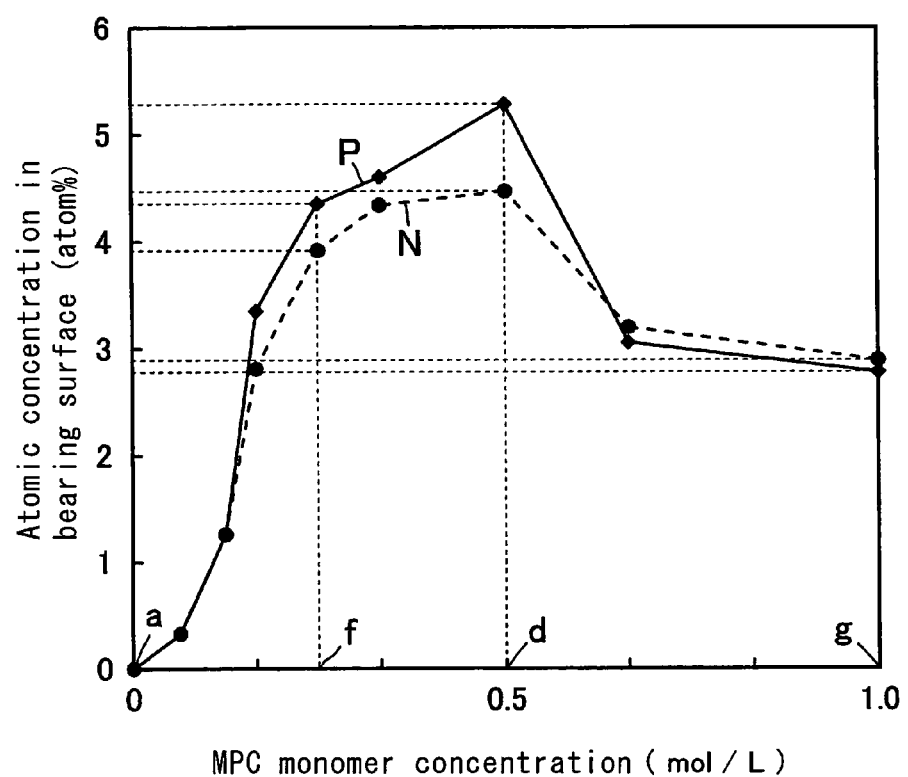
FIG. 21 is a graph showing the measurement results of an atomic concentration of phosphorus atom and an atomic concentration of nitrogen atom of the acetabular cup surface according to Example 4 of the present invention.

Measurement of Atomic Concentration of Phosphorus Atom and Atomic Concentration of Nitrogen Atom Atomic concentration of phosphorus atom and atomic concentration of nitrogen atom were measured by XPS analysis on various samples of different monomer concentrations, with the results shown in FIG. 21. Points a, d, f and g in the graph represent the test results of samples a, d, f and g, respectively, of Example 1. As can be seen from FIG. 21, it can be seen that atomic concentration of phosphorus atom (graph P) and atomic concentration of nitrogen atom (graph N) have similar tendencies. Atomic concentration of phosphorus atom and atomic concentration of nitrogen atom show the highest values when the monomer concentration is 0.5 mg/L. In the range of the monomer concentration from 0.25 to 0.50 mg/L where good hydrophilicity was obtained, atomic concentration of phosphorus atom was 4.3 atom % or higher and atomic concentration of nitrogen atom was 3.9 atom % or higher.

With a high monomer concentration of 0.75 mol/L or higher, atomic concentration of phosphorus atom and atomic concentration of nitrogen atom are low despite a large thickness of the MPC polymer layer. This is supposedly because density of the MPC polymer layer becomes lower due to the effect of pin holes.

EXAMPLE 5

Figure 22:
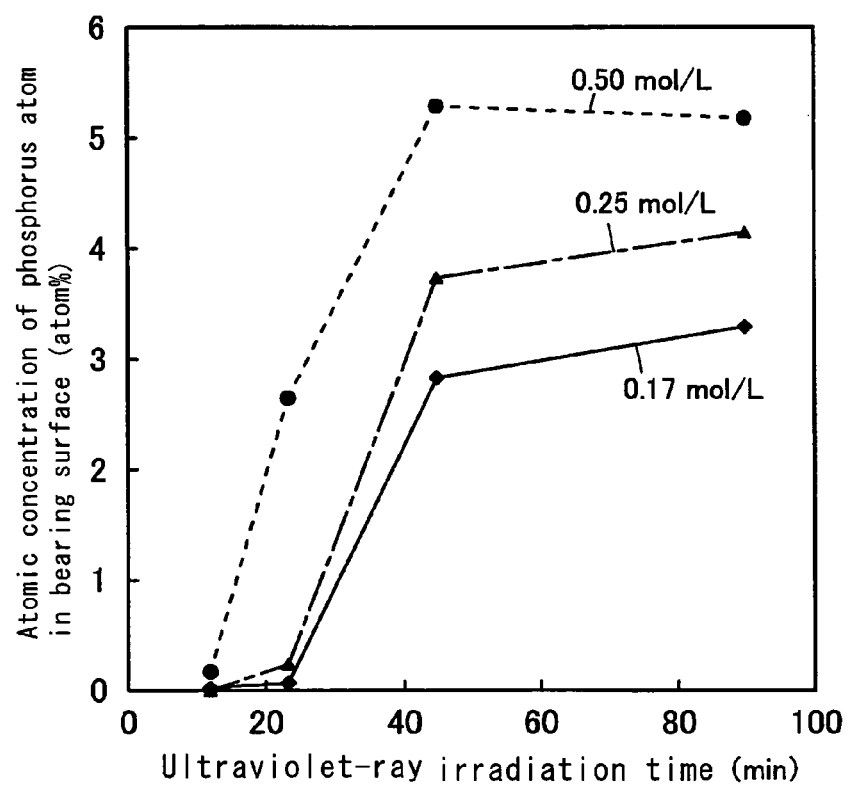
FIG. 22 is a graph showing the measurement results of an atomic concentration of phosphorus atom of an acetabular cup surface according to Example 5 of the present invention.

Changes in the influence of the ultraviolet-ray irradiation time on the MPC polymer layer with various monomer concentrations were investigated. In this Example, atomic concentration of phosphorus atom was measured as the indicator. Samples were prepared in a procedure similar to that of Example 1. Three kinds of monomer solution were prepared with monomer concentration of 0.17 mol/L, 0.25 mol/L and 0.50 mol/L, and the samples were prepared while changing the ultraviolet-ray irradiation time. The atomic concentration of phosphorus atom was measured by XPS analysis on various samples, with the results shown in FIG. 22. The atomic concentration of phosphorus atom showed substantially similar tendency to increase with all of the monomer concentrations. The atomic concentration of phosphorus atom increased roughly in proportion to the ultraviolet-ray irradiation time till 50 minutes where it stopped increasing. Thus it is supposed that formation of the MPC polymer layer is mostly completed with ultraviolet-ray irradiation of 50 minutes, regardless of the monomer concentration. When the monomer concentration is high, in particular, increasing rate of atomic concentration of phosphorus atom due to the ultraviolet-ray irradiation beyond the period of 50 minutes is lower than that of a case of lower monomer concentration, thus showing that the effect of ultraviolet-ray irradiation on the atomic concentration of phosphorus atom saturates at around 50 minutes. As shown in Example 1, it is preferable to set the ultraviolet-ray irradiation time to 40 minutes or more when the monomer concentration is 0.50 mol/L. For all values of the monomer concentration, it is preferable to irradiate with ultraviolet light for 50 minutes or more.

What is claimed is:

1. A high wear-resistance bearing material for being used under a humid environment comprising:
    a substrate made of a polymer material having a methylene repeating unit; and
    a polymer layer covering a bearing surface of the substrate, the polymer layer comprising polymer chains which have a phosphorylcholine group and are grafted from the bearing surface, wherein the polymer layer having the phosphorylcholine group has a static-water contact angle not greater than 20 degrees, and
    wherein a phosphoric index of a covered bearing surface covered with the polymer layer is not less than 0.28, the phosphoric index being calculated by dividing a peak intensity of a phosphate group of the polymer layer in an infrared spectrum measured on the covered bearing surface by a peak intensity of the methylene repeating unit of the bearing surface in the infrared spectrum.

2. The bearing material according to claim 1, wherein the phosphoric index is not less than 0.45.

3. The bearing material according to claim 1, wherein the polymer layer has a thickness of 10 to 200 nm.

4. The bearing material according to claim 1, wherein the polymer layer having the phosphorylcholine group has the static-water contact angle not greater than 14 degrees.

5. The bearing material according to claim 1, wherein an atomic concentration of phosphorus atom obtained by X-ray photoelectron spectroscopy of the covered bearing surface is not less than 4.7 atom %.

6. The bearing material according to claim 5, wherein the atomic concentration of phosphorus atom obtained by X-ray photoelectron spectroscopy of the covered bearing surface is not less than 5.3 atom %.

7. The bearing material according to claim 1, wherein an atomic concentration of nitrogen atom obtained by X-ray photoelectron spectroscopy of the covered bearing surface is not less than 3.6 atom %.

8. The bearing material according to claim 7, wherein the atomic concentration of nitrogen atom obtained by X-ray photoelectron spectroscopy of the covered bearing surface is not less than 4.6 atom %.

9. The bearing material according to claim 1, wherein the polymer layer is made of 2-methacryloyloxyethyl phosphorylcholine homopolymer.

10. The bearing material according to claim 1, wherein the polymer material having the methylene repeating unit which is used for forming the substrate is an ultra high molecular weight polyethylene having a molecular weight of not less than 3 million g/mol.

11. The bearing material according to claim 10, wherein the polymer material having the methylene repeating unit is a crosslinked polyethylene formed by crosslinking the ultra high molecular weight polyethylene.

12. The bearing material according to claim 11, wherein the substrate made of the polymer material having the methylene repeating unit contains a free radical.

13. The bearing material according to claim 1, wherein the bearing material constitutes a polymer bearing component for an artificial joint including an artificial hip joint, an artificial shoulder joint, an artificial vertebral joint, an artificial knee joint, an artificial elbow joint, an artificial ankle joint, an artificial finger joint and an artificial disk.

14. An artificial joint comprising:
    the polymer bearing component for the artificial joint according to claim 13; and a corresponding component made of a ceramic or a metal against the polymer bearing component.

15. The artificial joint according to claim 14, wherein the artificial joint is the artificial hip joint, the artificial shoulder joint or the artificial vertebral joint,
the polymer bearing component for the artificial joint being a cup part having a spherical covered bearing surface, and
the corresponding component being a femoral head part slidably received in the covered bearing surface of the cup part or in slidable contact with the covered bearing surface thereof.

16. The artificial joint according to claim 14, wherein the artificial joint is the artificial knee joint, the artificial elbow joint or the artificial ankle joint,
the polymer bearing component for the artificial joint being a tray part having a curved, covered bearing surface, and
the corresponding component being a joint part in slidable contact with the covered bearing surface of the tray part.

17. The artificial joint according to claim 14, wherein the artificial joint is the artificial finger joint, the artificial knee joint or the artificial elbow joint, all of which have a hinge structure,
the corresponding member being a shaft component having a shaft part both ends of which project, and
the bearing component being a bearing part having bearing holes in which the ends of the shaft part are fitted slidably.

18. A method of producing the bearing material claimed in claim 1, the method comprising steps of:
forming the substrate made of the polymer material having the methylene group; and
forming the polymer layer on the bearing surface of the substrate by being grafted from the bearing surface with the polymer chains having the phosphorylcholine group,
the step of forming the polymer layer comprising processes of:
applying a photoinduced polymerization initiator on the bearing surface of the substrate; and
irradiating the bearing surface of the substrate with a ultraviolet light having an sufficient intensity so as to excite the photoinduced polymerization initiator in a state of being immersed in a solution containing a polymerizable monomer having the phosphorylcholine group,
wherein the solution including the polymerizable monomer has a monomer concentration of 0.25 to 0.50 mol/L, and
wherein an ultraviolet-ray irradiation time is not less than 40 minutes.

19. The method according to claim 18, wherein an ultraviolet-ray irradiation time from 45 to 90 minutes in the process of exposing to the ultraviolet light in the step of forming the polymer layer.

20. The method according to claim 18, wherein the ultraviolet-ray irradiation time is not less than 80 minutes in the process of irradiating with ultraviolet light in the step of forming the polymer layer.

21. The method according to claim 18, further comprising the step of irradiating the bearing surface of the substrate with a gamma-ray after the step of forming the polymer layer.

22. The method according to claim 18, wherein the step of forming the substrate is a step of shaping an irradiated polymer material into the substrate, the irradiated polymer material being the polymer material having the methylene group previously irradiated with a high energy beam.

23. The method according to claim 22, further comprising a step of preparing the irradiated polymer material having the methylene group previously irradiated with the high energy beam before the step of shaping the irradiated polymer material,
the step of preparing the irradiated polymer material comprising processes of:
irradiating the polymer material having the methylene group with a gamma-ray; and
heat-treating the polymer material irradiated with the gamma-ray below a melting point of the polymer material.

24. The bearing material according to claim 1, wherein the phosphoric index is not less than 0.32.

* * * * *